(12) United States Patent
Mosler et al.

(10) Patent No.: US 9,345,640 B2
(45) Date of Patent: May 24, 2016

(54) FLUID TRANSFER DEVICE

(75) Inventors: Theodore J. Mosler, Raleigh, NC (US);
Bryan J. Peters, Raleigh, NC (US);
David L. Foshee, Apex, NC (US)

(73) Assignee: YUKON MEDICAL, LLC, Durham, NC (US)

( * ) Notice: Subject to any disclaimer, the term of this patent is extended or adjusted under 35 U.S.C. 154(b) by 1174 days.

(21) Appl. No.: 13/264,614

(22) PCT Filed: Apr. 14, 2010

(86) PCT No.: PCT/US2010/031124
§ 371 (c)(1),
(2), (4) Date: Dec. 9, 2011

(87) PCT Pub. No.: WO2010/120953
PCT Pub. Date: Oct. 21, 2010

(65) Prior Publication Data
US 2012/0067429 A1 Mar. 22, 2012

Related U.S. Application Data

(60) Provisional application No. 61/294,824, filed on Jan. 13, 2010, provisional application No. 61/212,652, filed on Apr. 14, 2009.

(51) Int. Cl.
*A61J 1/20* (2006.01)
*B65D 51/00* (2006.01)
(Continued)

(52) U.S. Cl.
CPC .............. *A61J 1/2089* (2013.01); *B65D 51/002* (2013.01); *A61J 1/10* (2013.01); *A61J 1/1418* (2015.05);
(Continued)

(58) Field of Classification Search
CPC ...... A61J 1/2089; B65D 51/002; B65D 21/02
USPC ............ 137/318, 1; 251/149.1; 604/411, 246, 604/32
See application file for complete search history.

(56) References Cited

U.S. PATENT DOCUMENTS 2,584,397 A   2/1952  Pitman
4,175,559 A   11/1979 Kreb
(Continued)

FOREIGN PATENT DOCUMENTS

EP   521460 B1   9/1995
EP   570939 B1   8/1998
(Continued)

OTHER PUBLICATIONS

Korean Intellectual Property Office, PCT International Search Report and Written Opinion for International Application No. PCT/US2010/031124 dated Jan. 17, 2011.
(Continued)

*Primary Examiner* — Kevin Lee
(74) *Attorney, Agent, or Firm* — Christopher J. Knors; Moore & Van Allen PLLC

(57) ABSTRACT

A fluid transfer device comprising a housing and a flow controller at least partially slidably disposed in the housing, the flow controller comprising at least one fluid channel and a vent conduit. A shroud, alone or in combination with the fluid transfer device comprising a plurality of segments terminating in a annular edge and defining a plurality of openings, and a plurality of protrusions, each of the plurality of protrusions having a proximal end connected to the annular edge and a distal end positioned in one of the plurality of openings adapted for the housing of the fluid transfer device is provided.

18 Claims, 15 Drawing Sheets

(51) Int. Cl.
   *A61J 1/10* (2006.01)
   *A61J 1/22* (2006.01)
   *A61M 39/22* (2006.01)

(52) U.S. Cl.
   CPC ............... *A61J 1/201* (2015.05); *A61J 1/2013* (2015.05); *A61J 1/2055* (2015.05); *A61J 1/2058* (2015.05); *A61J 1/2062* (2015.05); *A61J 1/2075* (2015.05); *A61J 1/2082* (2015.05); *A61J 1/22* (2013.01); *A61M 39/223* (2013.01); *Y10T 137/0318* (2015.04); *Y10T 137/1632* (2015.04); *Y10T 137/8158* (2015.04); *Y10T 137/8593* (2015.04)

(56) References Cited

U.S. PATENT DOCUMENTS

| | | | |
|---|---|---|---|
| 4,532,969 | A | 8/1985 | Kwaan |
| 4,729,401 | A | 3/1988 | Raines |
| 4,759,756 | A | 7/1988 | Forman et al. |
| 4,863,454 | A | 9/1989 | LaBove |
| 4,921,490 | A | 5/1990 | Spier et al. |
| 4,994,029 | A | 2/1991 | Rohrbough |
| 4,997,430 | A | 3/1991 | Van der Heiden et al. |
| 5,088,996 | A | 2/1992 | Kopfer et al. |
| 5,152,965 | A | 10/1992 | Fisk et al. |
| 5,232,029 | A | 8/1993 | Knox et al. |
| 5,257,650 | A | 11/1993 | Fisk et al. |
| 5,279,576 | A | 1/1994 | Loo et al. |
| 5,297,433 | A | 3/1994 | Elgas |
| 5,304,163 | A | 4/1994 | Bonnici et al. |
| 5,304,165 | A | 4/1994 | Haber et al. |
| 5,329,976 | A | 7/1994 | Haber et al. |
| 5,334,163 | A | 8/1994 | Sinnett |
| 5,352,191 | A | 10/1994 | Sunago et al. |
| 5,397,303 | A | 3/1995 | Sancoff et al. |
| 5,423,753 | A | 6/1995 | Fowles et al. |
| 5,445,631 | A | 8/1995 | Uchida |
| 5,464,123 | A | 11/1995 | Scarrow |
| 5,466,220 | A | 11/1995 | Brenneman |
| 5,520,659 | A | 5/1996 | Hedges |
| 5,522,804 | A | 6/1996 | Lynn |
| 5,526,853 | A | 6/1996 | McPhee et al. |
| 5,527,306 | A | 6/1996 | Hawing |
| 5,554,128 | A | 9/1996 | Hedges |
| 5,562,616 | A | 10/1996 | Haber et al. |
| 5,599,302 | A | 2/1997 | Lilley et al. |
| 5,636,660 | A | 6/1997 | Pfleiderer et al. |
| 5,641,010 | A | 6/1997 | Maier |
| 5,685,845 | A | 11/1997 | Grimard |
| 5,743,312 | A | 4/1998 | Pfeifer et al. |
| 5,766,147 | A | 6/1998 | Sancoff et al. |
| 5,776,124 | A | 7/1998 | Wald |
| 5,833,213 | A | 11/1998 | Ryan |
| 5,957,891 | A | 9/1999 | Kriesel et al. |
| 6,003,566 | A | 12/1999 | Thibault et al. |
| 6,063,068 | A | 5/2000 | Fowles et al. |
| 6,139,534 | A | 10/2000 | Niedospial et al. |
| 6,209,738 | B1 | 4/2001 | Jansen et al. |
| 6,237,649 | B1 | 5/2001 | Moisio et al. |
| 6,238,372 | B1 | 5/2001 | Zinger et al. |
| 6,355,023 | B1 | 3/2002 | Roth et al. |
| 6,364,865 | B1 | 4/2002 | Lavi et al. |
| 6,379,340 | B1 | 4/2002 | Zinger et al. |
| 6,409,708 | B1 | 6/2002 | Wessman |
| 6,453,956 | B2 | 9/2002 | Safabash |
| 6,474,375 | B2 | 11/2002 | Spero et al. |
| 6,551,299 | B2 | 4/2003 | Miyoshi et al. |
| 6,558,365 | B2 | 5/2003 | Zinger et al. |
| 6,571,837 | B2 | 6/2003 | Jansen et al. |
| 6,645,171 | B1 | 11/2003 | Robinson et al. |
| 6,656,433 | B2 | 12/2003 | Sasso |
| 6,699,229 | B2 | 3/2004 | Zinger et al. |
| 6,752,180 | B2 | 6/2004 | Delay |
| 6,852,103 | B2 | 2/2005 | Fowles et al. |
| 6,875,203 | B1 | 4/2005 | Fowles et al. |
| 6,875,205 | B2 | 4/2005 | Leinsing |
| 6,890,328 | B2 | 5/2005 | Fowles et al. |
| 6,948,522 | B2 | 9/2005 | Newbrough et al. |
| 7,074,216 | B2 | 7/2006 | Fowles et al. |
| 7,077,835 | B2 | 7/2006 | Robinson et al. |
| 7,140,401 | B2 | 11/2006 | Wilcox et al. |
| 7,294,122 | B2 | 11/2007 | Kubo et al. |
| 7,326,194 | B2 | 2/2008 | Zinger et al. |
| 7,491,197 | B2 | 2/2009 | Jansen et al. |
| 7,879,018 | B2 * | 2/2011 | Zinger et al. .................. 604/410 |
| 8,225,949 | B2 * | 7/2012 | Aneas ........................ 215/249 |
| 8,562,582 | B2 * | 10/2013 | Tuckwell et al. ............. 604/406 |
| 8,714,384 | B2 * | 5/2014 | Aneas ........................ 215/364 |
| 8,753,325 | B2 * | 6/2014 | Lev et al. .................... 604/405 |
| 2002/0087144 | A1 | 7/2002 | Zinger |
| 2002/0127150 | A1 | 9/2002 | Sasso |
| 2004/0225274 | A1 | 11/2004 | Jansen et al. |
| 2004/0249341 | A1 | 12/2004 | Newbrough et al. |
| 2005/0148994 | A1 * | 7/2005 | Leinsing ...................... 604/414 |
| 2006/0025751 | A1 | 2/2006 | Roy |
| 2007/0088313 | A1 | 4/2007 | Zinger et al. |
| 2008/0172024 | A1 | 7/2008 | Yow |
| 2008/0177244 | A1 | 7/2008 | Capitaine |
| 2009/0054834 | A1 | 2/2009 | Zinger et al. |
| 2009/0082750 | A1 | 3/2009 | Denenburg et al. |
| 2009/0127288 | A1 | 5/2009 | Keller |
| 2010/0179506 | A1 | 7/2010 | Shemesh et al. |

FOREIGN PATENT DOCUMENTS

| | | | |
|---|---|---|---|
| EP | 737484 | B1 | 8/2002 |
| EP | 1192966 | B1 | 11/2005 |
| EP | 1145702 | B1 | 5/2010 |
| JP | 2005-518907 | | 6/2005 |
| JP | 2008-544840 | | 12/2008 |
| JP | 2012515055 | A | 7/2012 |
| WO | WO9629113 | A1 | 9/1996 |
| WO | WO9720536 | A1 | 6/1997 |
| WO | WO0149361 | A1 | 7/2001 |
| WO | WO 2007/000066 | A1 | 1/2007 |
| WO | WO 2007/063218 | A1 * | 6/2007 |
| WO | WO2009026443 | A3 | 4/2009 |
| WO | WO2009146088 | A | 12/2009 |

OTHER PUBLICATIONS

Australian Government—IP Australia, Australian Patent Examination Report for Australian Application No. 2010236426 dated Aug. 29, 2012.

Japanese Patent Office; Japanese Patent Application No. 2012-506191 Office Action dated Mar. 28, 2014, pp. 1-9.

The International Bureau of WIPO, PCT International Preliminary Report on Patentability and Written Opinion of the International Searching Authority for International Application No. PCT/US2010/031124 datged Oct. 18, 2011.

European Patent Office, European Patent Application No. 10765142.4 Supplementary European Search Report dated Oct. 2, 2014, 7 pages.

Japanese Patent Office; Office Action for Japanese Patent Application No. 2015-004901 dated Dec. 15, 2015, 8 pages.

* cited by examiner

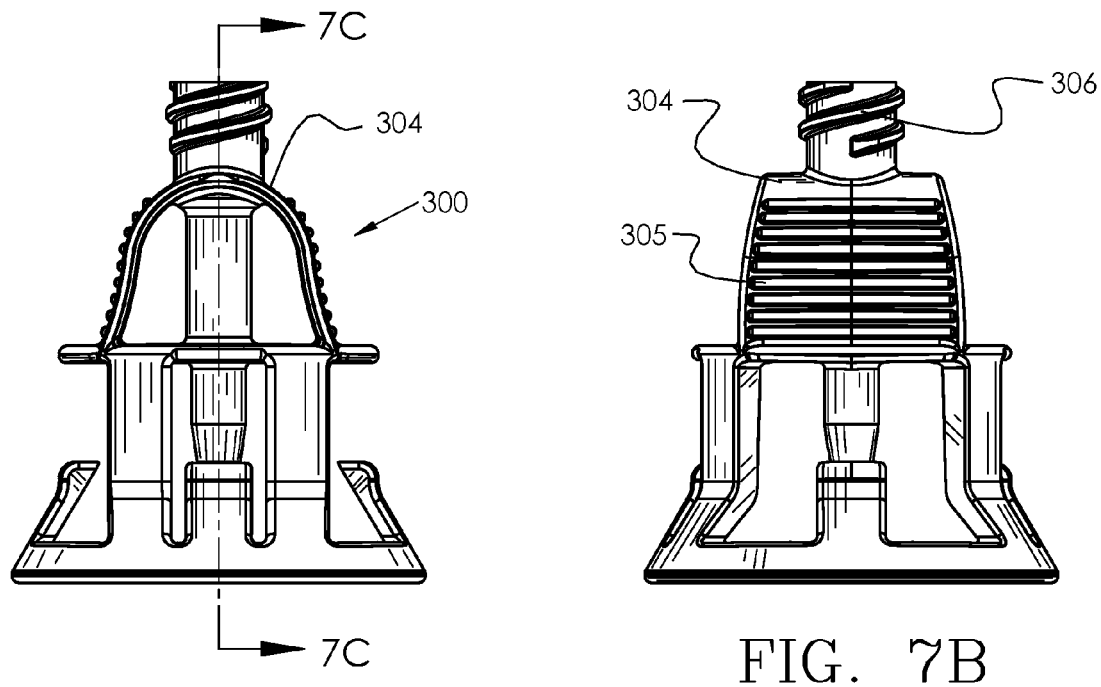
FIG. 7A
FIG. 7B
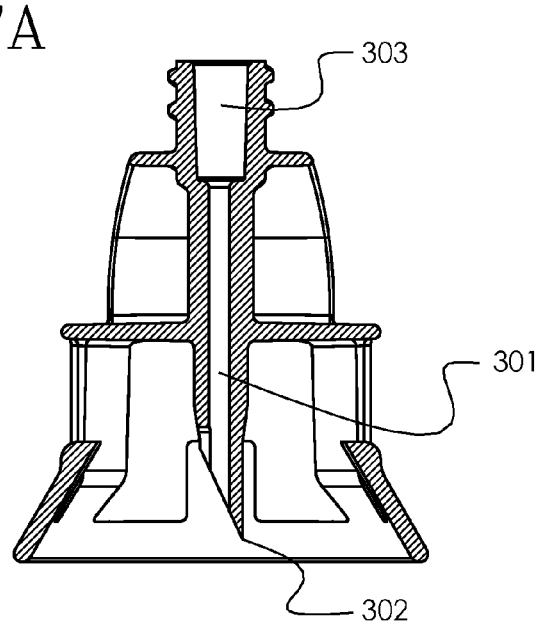
FIG. 7C

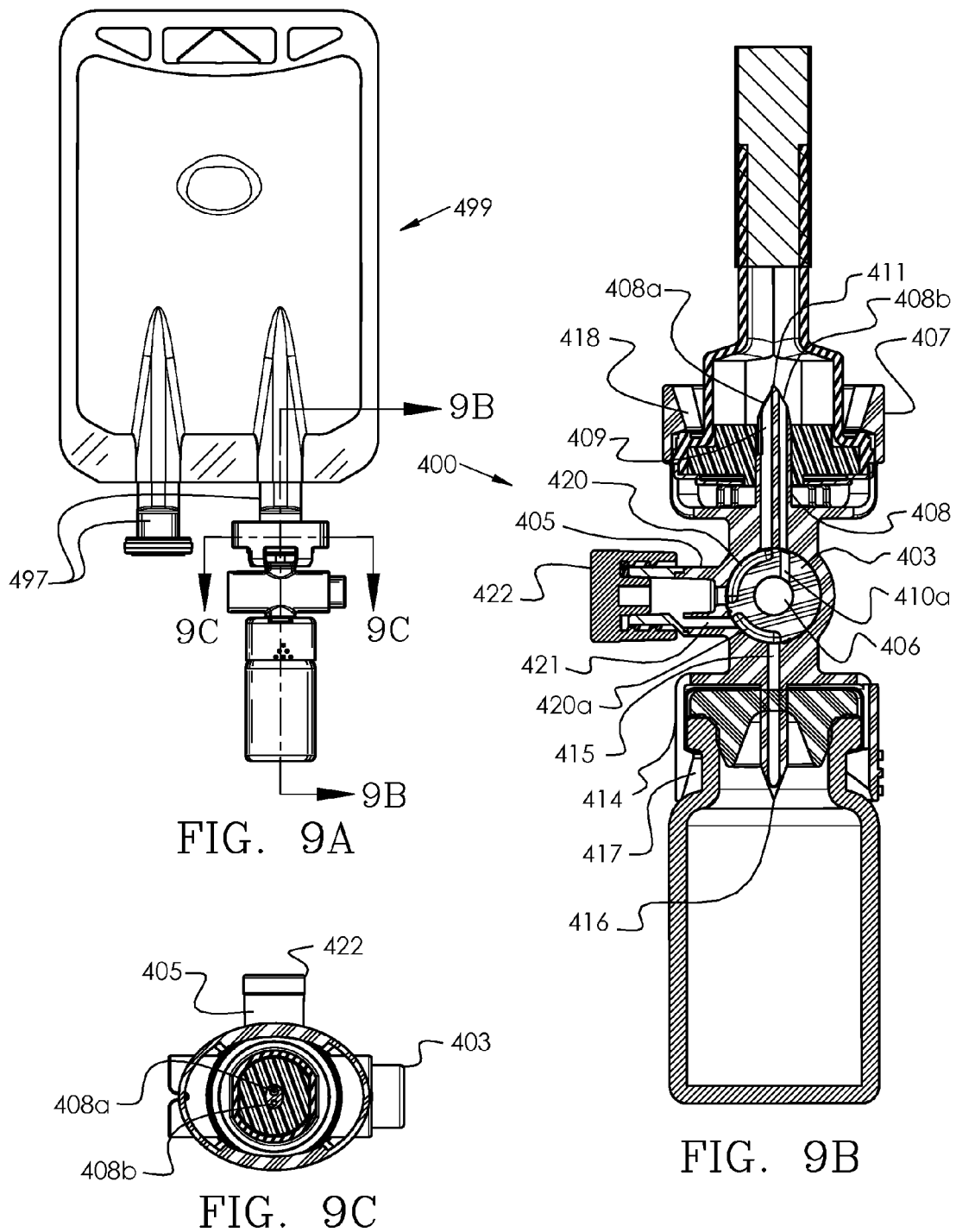

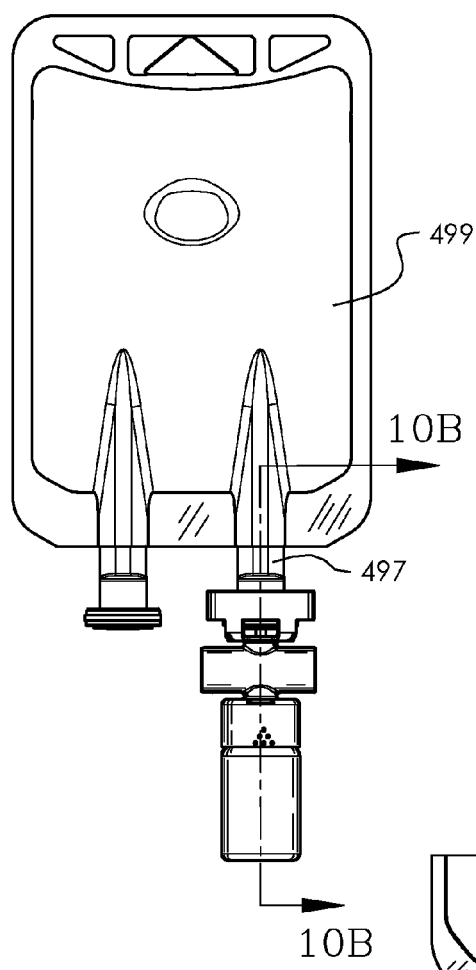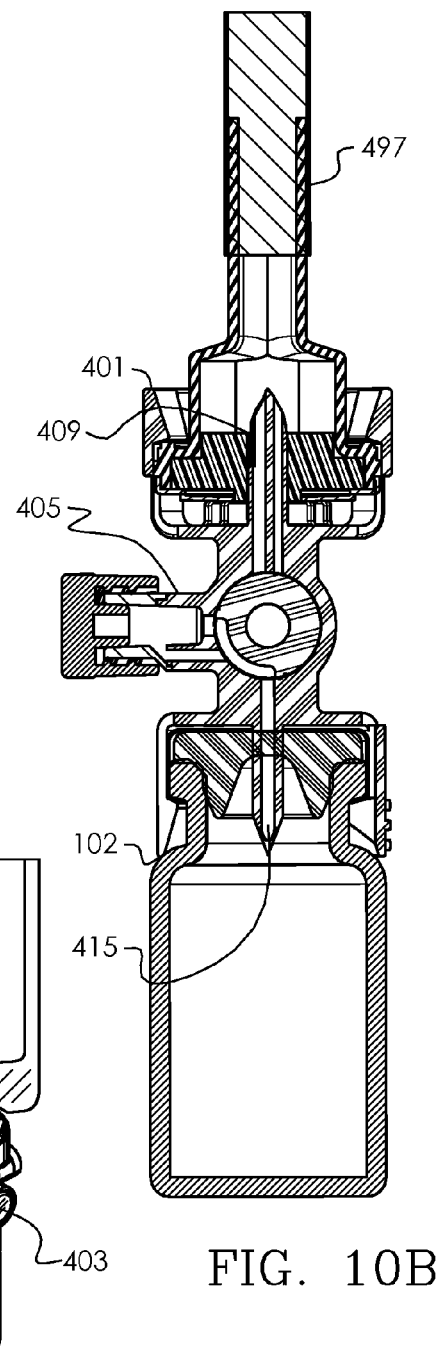
FIG. 10A
FIG. 10C
FIG. 10B

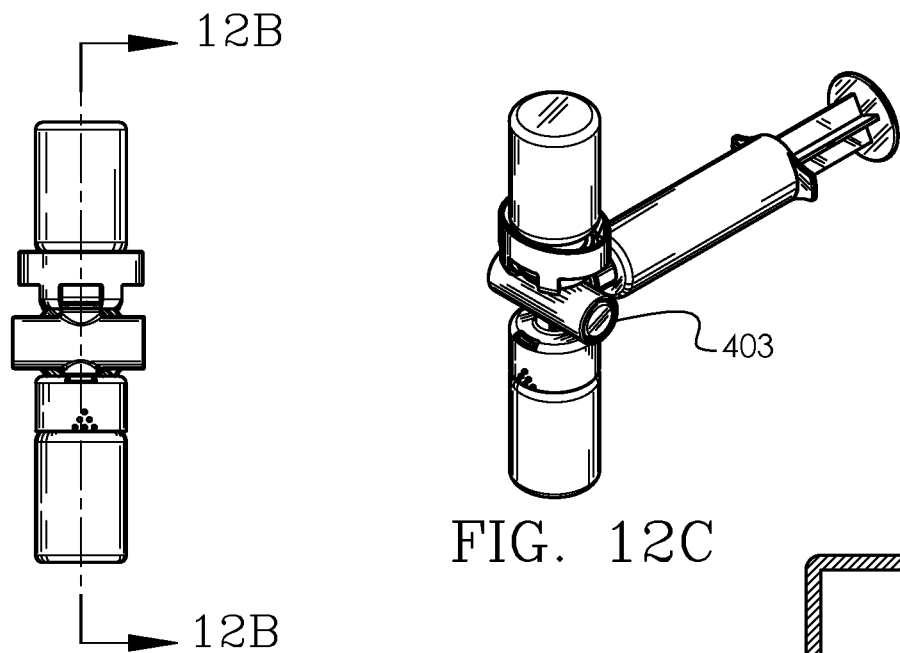
FIG. 12C
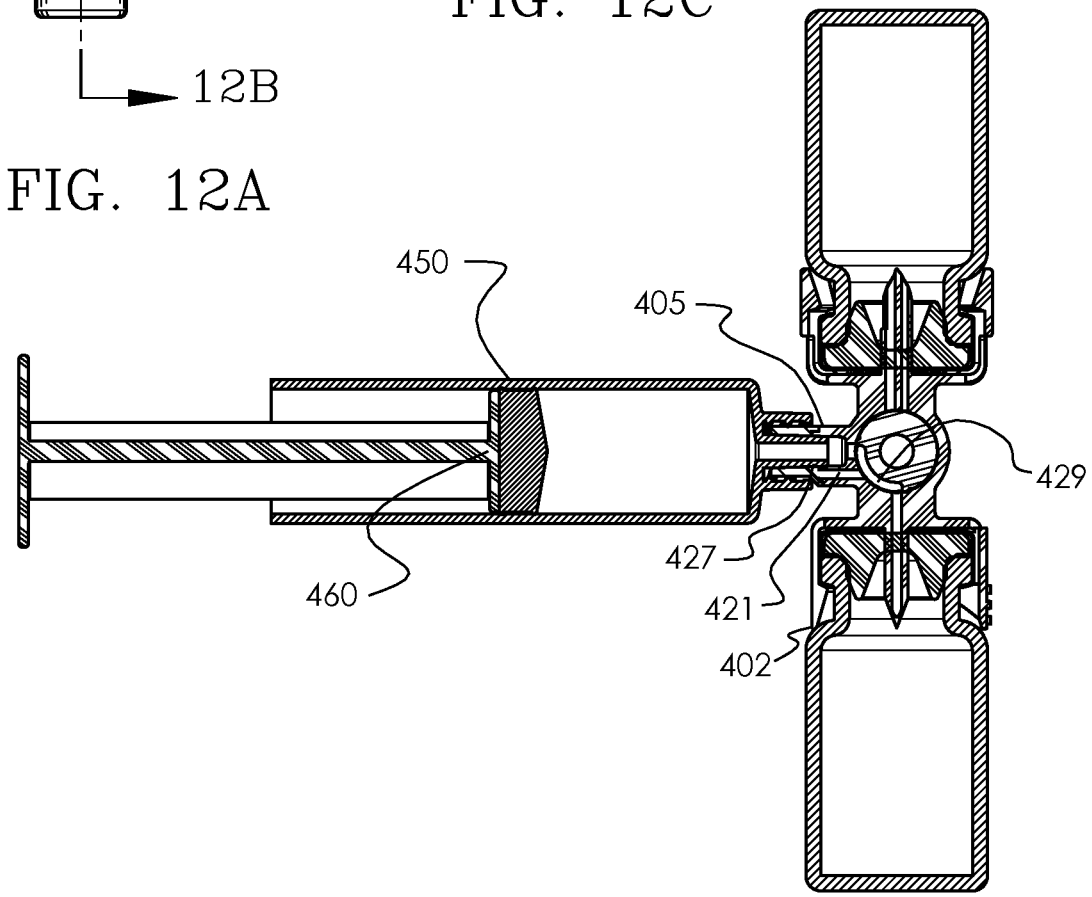
FIG. 12A
FIG. 12B

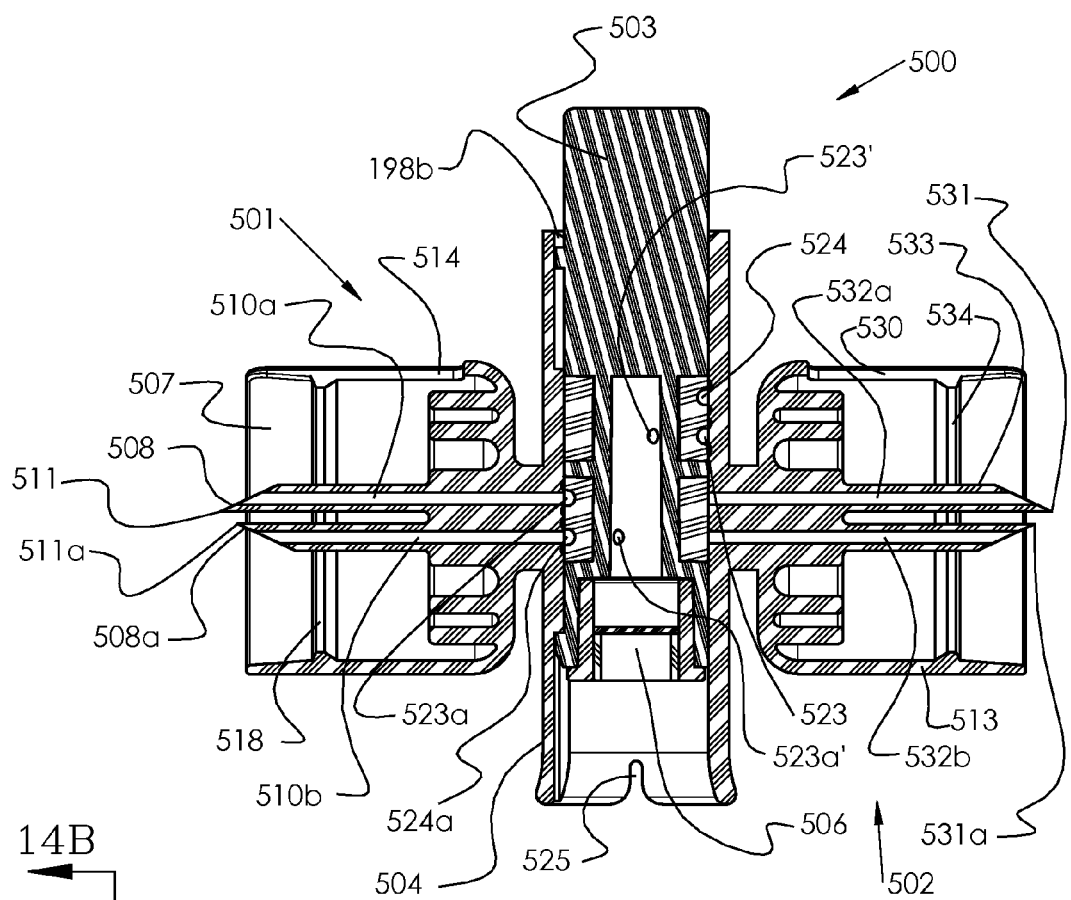
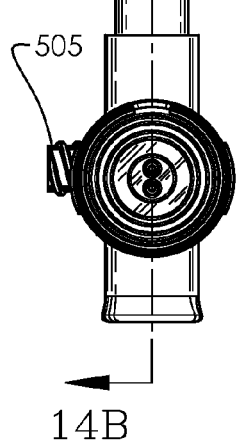
FIG. 14A
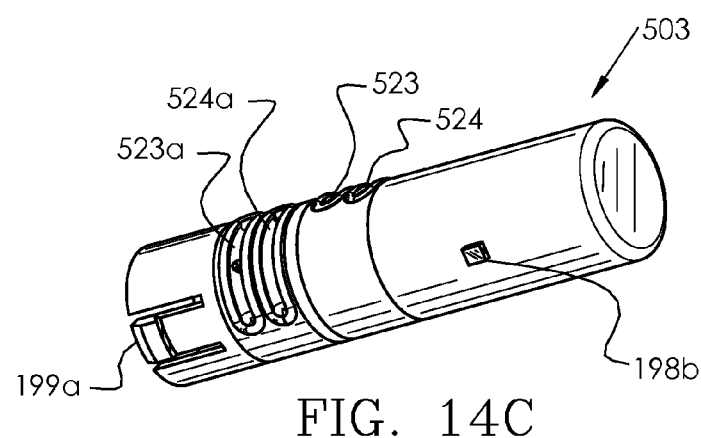
FIG. 14C

FLUID TRANSFER DEVICE

CROSS-REFERENCE TO RELATED APPLICATIONS

This application is filed under the provisions of 35 U.S.C. §371 and claims the benefit of International Patent Application No. PCT/2010/031124, filed on Apr. 14, 2010 entitled "FLUID TRANSFER DEVICE", which claims the benefit of priority of U.S. Provisional Patent Application Nos. 61/294,824, filed on Jan. 13, 2010 and U.S. Provisional Patent Application No. 61/212,652, filed on Apr. 14, 2009, all of which are hereby incorporated by reference herein in their entirety.

FIELD OF INVENTION

The invention relates to a fluid transfer device, for example for medical fluids, with a housing, access means associated with the housing for transfer of fluid from the transfer device, a piercing assembly associated with the housing, and alone or in combination, a shroud for retaining or securing a container to the housing.

BACKGROUND

In medical technology, it may be necessary to transfer a substance from a first container, for example a container, a vial or an IV bag, to a second container, for example a vial or an IV bag for dissolution or suspension and possibly the withdraw of the dissolved or suspended material back into one of the containers or to a fluid delivery device, such as a syringe.

Drugs intended for parenteral administration are typically stored in a sealed container either as a dry powder, liquid concentrate, suspension, or as a solution. The contents of the container may also be immediately used with a physiological solution prior to administration in a similar manner to a dry powder drug. The physiological solution can be provided via a pre-filled syringe or vial, IV bag, or other medicinal vessel.

Sealed containers typically fall into one of three categories. The first type is a vial or a glass bottle closed by a rubber stopper which can be penetrated by a puncturing element, and which is self-closing upon withdrawal of the puncturing device. Such a vial or glass bottle can contain a single dose or a multiple dose of a drug. The drug contained in such a vial can be under reduced pressure. The second type of container is an ampoule whose top portion is broken off enabling access to its contents. The third type is an IV bag provided with a sample port for accessing its contents. The sample port can be of the pre-slit septum type or may require puncturing.

Typically, a transfer device with a piercing element is inserted into the rubber or other closures, respectively, providing communication between the two containers. The transfer of the fluid may be assisted by the fact that there is a vacuum in the inside of the container containing the substance to be dissolved or diluted. Other flow lumens may be present and may be routed through the piercing members, to facilitate pressure compensation between the two containers, if there is no vacuum in the container or if the user does not correctly assemble the containers with the transfer device. The transfer of the fluid typically takes place with the fluid-containing container located above the container with the substance to be dissolved or suspended, so that the fluid can enter with gravitational assistance. Unfortunately, conventional transfer devices fall short of providing simple fluid transfer, for a variety of reasons, some of which include improper use of the device, loss of vacuum in the drug-containing vessel, exposure to vapors created by the rapid equilibration of pressure, etc.

Regardless of the manner in which a drug is stored, there is a continuous need to transfer fluid under sterile conditions before its administration to a patient. When a prior dilution of a drug is required, the process requires at least two fluid transfers. The problem of ensuring proper fluid transfer under aseptic conditions and without the accidental release of aerosols associated with the drug or its solution is especially acute in the case of chemotherapeutic drugs or for self-administration by users in their domiciles.

SUMMARY

In a first embodiment, a fluid transfer device is provided. The device comprises a housing adapted to receive a fluid container and a media container and a flow controller having an interior and an exterior, the flow controller at least partially slidably disposed in the housing, the flow controller comprising integral therewith, at least one fluid channel and at least one vent conduit.

In a first aspect of the first embodiment, the device further comprises a connector coupled to the housing, the connector adapted to receive a fluid delivery device, preferably a syringe.

In a second aspect, alone or in combination with any one of the previous aspects of the first embodiment, any of the at least one fluid channels is positioned about the perimeter of the flow controller exterior.

In a third aspect, alone or in combination with any one of the previous aspects of the first embodiment, the vent conduit is in fluid communication with the interior of the flow controller.

In a fourth aspect, alone or in combination with any one of the previous aspects of the first embodiment, the device further comprises a vent coupled to the flow controller.

In a fifth aspect, alone or in combination with any one of the previous aspects of the first embodiment, the flow controller comprises a first fluid channel and a second fluid channel, wherein the flow controller is configured to slidably move between: (i) a first predetermined position wherein the first fluid channel provides fluid communication between the connector, optionally the vent conduit, and the fluid container, and optionally the vent conduit, or (ii) a second predetermined position, wherein the second fluid channel provides fluid communication between the connector and the media container, and optionally the vent conduit. In a preferred aspect, in the first predetermined position, the first fluid channel provides fluid communication only between the connector, optionally the vent conduit, and the fluid container, or in the second predetermined position, the second fluid channel provides fluid communication only between the connector and the media container, and optionally the vent conduit.

In a sixth aspect, alone or in combination with any one of the previous aspects of the first embodiment, the flow controller provides metering of a predetermined amount of fluid from the fluid container via the connector.

In a seventh aspect, alone or in combination with any one of the previous aspects of the first embodiment, the device further comprises a fluid container accessing assembly associated with the housing, the fluid container accessing assembly adapted for accessing the fluid container, the fluid container accessing assembly comprising a fluid piercing member having at least one lumen.

In an eighth aspect, alone or in combination with any one of the previous aspects of the first embodiment, the device further comprises a media container piercing assembly associated with the housing, the media container accessing assembly adapted for accessing the media container, the media container accessing assembly comprising a media piercing member having at least one lumen.

In a ninth aspect, alone or in combination with any one of the previous aspects of the first embodiment, the at least one lumen of the fluid container piercing member is fluidically coupled to the vent conduit of the flow controller, optionally in combination with a check valve or filter.

In a tenth aspect, alone or in combination with any one of the previous aspects of the first embodiment, the flow controller includes two pairs of flow conduits partially circumscribing the perimeter of the flow controller, the two pairs of flow conduits being positioned in an offset relationship about the exterior of the flow controller.

In an eleventh aspect, alone or in combination with any one of the previous aspects of the first embodiment, the device further comprises a piercing assembly associated with the housing, the piercing assembly consisting of two piercing members each piercing member having at least one lumen, wherein one of the two pairs of flow conduits provides fluid communication between the at least one lumen of the two piercing members and one of the connector or the container. In a preferred aspect, only one of the two pairs of flow conduits provides fluid communication between the at least one lumen of the two piercing members, the connector and one of the fluid or media container.

In a twelfth aspect, alone or in combination with any one of the previous aspects of the first embodiment, the flow controller is restricted or prevented from rotation relative to the housing.

In a thirtieth aspect, alone or in combination with any one of the previous aspects of the first embodiment, the flow controller is restricted or prevented from slidably releasing from the housing.

In a second embodiment, a container accessing assembly is provided. The container accessing assembly comprises a housing having at least one shroud projecting from the housing, the shroud comprising a plurality of segments terminating in a annular edge, the plurality of segments and the annular edge defining a plurality of openings. A plurality of protrusions, each of the plurality of protrusions having a proximal end, is connected to the annular edge and a distal end thereof is positioned in one of the plurality of openings and inwardly extends towards the housing. The plurality of protrusions together with the annular edge defines a receiving volume sized to accommodate the closure portion of a container.

In first aspect of the second embodiment, the plurality of protrusions is in a fixed position with respect to the annular edge.

In a second aspect, alone or in combination with any one of the previous aspects of the second embodiment, the at least one of the protrusions has a tapered edge at the distal end thereof.

In a third aspect, alone or in combination with any one of the previous aspects of the second embodiment, the plurality of protrusions has a tapered edge at the distal end thereof.

In a fourth aspect, alone or in combination with any one of the previous aspects of the second embodiment, the tapered edge tapers outward proximate the distal end of the protrusion.

In a fifth aspect, alone or in combination with any one of the previous aspects of the second embodiment, a distance is maintained between the distal end of the protrusion and housing and the distance is dimensioned to allow for receiving a closure portion of a container.

In a sixth aspect, alone or in combination with any one of the previous aspects of the second embodiment, a distance is maintained between the plurality of segments and the plurality of protrusions, and wherein the distance is dimensioned to allow the protrusions to flex when receiving a closure portion of a container.

In a seventh aspect, alone or in combination with any one of the previous aspects of the second embodiment, the plurality of segments are substantially parallel relative to each other.

In an eighth aspect, alone or in combination with any one of the previous aspects of the second embodiment, the plurality of openings and the plurality of segments each total four.

In a ninth aspect, alone or in combination with any one of the previous aspects of the second embodiment, the annular edge is continuous.

In a third embodiment, a shroud for connecting to a vial having a closure portion is provided. The shroud comprises a housing, a plurality of segments terminating in a annular edge and defining a plurality of openings, a plurality of protrusions circumferentially spaced and inwardly extending from the annular edge, the protrusions defining a receiving volume dimensioned to receive the closure portion of the vial. The protrusions have a proximal end connected to the annular edge and a distal end positioned in the opening, whereby the protrusions deflect outwardly away from an initial position during contact and traversing of the closure portion of the vial and return to approximately their initial position when the closure portion of the vial passes the distal end of the protrusion. And, the protrusions deflect inwardly towards the closure portion of the vial when a removing force is applied to the vial, thereby preventing removal of the vial.

In a first aspect of the third embodiment, the housing comprises a pair of each of the plurality of segments and the plurality of protrusions.

In a second aspect, alone or in combination with any one of the previous aspects of the third embodiment, the pair of each of the plurality of segments and the plurality of protrusions are opposed about the housing.

In a fourth embodiment, a fluid transfer device is provided. The device, comprises a housing adapted to receive a fluid container and a media container, a flow controller having an interior and an exterior, the flow controller at least partially slidably disposed in the housing, the flow controller comprising at least one flow conduit, at least one vent conduit, and a vent. A connector is coupled to the housing and configured for fluid communication with the at least one flow conduit of the flow controller, and at least one shroud projects from the housing. The shroud comprises a plurality of segments terminating in an annular edge and defining a plurality of openings. A plurality of protrusions, each of the plurality of protrusions proximally projecting from the annular edge and terminating at a distal end positioned in one of the plurality of openings, the distal ends inwardly extending towards the housing. The plurality of protrusions together with the annular edge defines a receiving volume sized to accommodate the closure portion of one of the fluid container or the media container. The flow controller is configured to slidably move between a first predetermined position where fluid communication is provided between the at least one fluid conduit, the vent conduit, and the fluid container and the connector, and a second predetermined position wherein the at least one flow conduit provides fluid communication between the media container and the connector. In a preferred aspect, the flow controller is configured to slidably move between a first predetermined position where fluid communication is provided between the at least one fluid conduit, the vent conduit, and only the fluid container and the connector, and a second predetermined position wherein the at least one flow conduit provides fluid communication between only the media container and the connector.

In a first aspect of the fourth embodiment, the vent conduit is in fluid communication with the interior of the flow controller.

In a second aspect, alone or in combination with any one of the previous aspects of the fourth embodiment, the vent conduit is in fluid communication with a vent integral positioned within the interior of the flow controller.

In a third aspect, alone or in combination with any one of the previous aspects of the fourth embodiment, the flow controller is restricted or prevented from rotation relative to the housing.

In a fourth aspect, alone or in combination with any one of the previous aspects of the fourth embodiment, the flow controller is restricted or prevented from slidably releasing from the housing.

In a fifth aspect, alone or in combination with any one of the previous aspects of the fourth embodiment, the device further comprises a fluid container accessing assembly associated with the housing, the fluid container accessing assembly adapted for accessing the fluid container. The fluid container accessing assembly comprises a fluid piercing member and at least one fluid lumen, optionally in combination with a vent lumen and/or a filter. A media container accessing assembly is associated with the housing, the media container accessing assembly adapted for accessing the media container, the media container accessing assembly comprises a media piercing member and at least one fluid lumen.

In a sixth aspect, alone or in combination with any one of the previous aspects of the fourth embodiment, the device further comprises a removable member adapted to engage the flow controller such that the flow controller is prevented from moving to the second predetermined position.

In a fifth embodiment, a method of transferring material among containers is provided. The method comprises providing a fluid transfer device, the device comprising a housing adapted to receive a fluid container, and a flow controller at least partially slidably disposed in the housing. The flow controller comprising a connector, at least one fluid channel, and at least one vent conduit. Receiving at least one container to the housing of the fluid transfer device, and slidably positioning the flow controller to provide fluidic communication between the at least one fluid channel and the at least one vent conduit and the fluid container.

In a first aspect of the fifth embodiment, the housing is adapted to receive a media container comprising a pharmaceutical in the form of a solid, liquid, suspension, or combinations thereof.

In a second aspect, alone or in combination with any one of the previous aspects of the fifth embodiment, the flow controller is configured within the housing and slidably disposable to one of the following positions: (i) a first position wherein the at least one fluid channel and at least one vent conduit are in fluid communication with the fluid container, the vent conduit, and the connector; or, (ii) a second position wherein the at least one fluid channel is in fluid communication with the media container and with the connector, and not in fluid communication with the at least one vent conduit.

In a third aspect, alone or in combination with any one of the previous aspects of the fifth embodiment, the flow controller is configured with at least one vent integral therewith, the at least one vent fluidically coupled to at least one of the fluid container and/or the media container.

BRIEF DESCRIPTION OF THE DRAWINGS

FIGS. 7A, 7B & 7C depict a front view, a side view and a section view, respectively, of a third aspect of a ring shroud.

FIGS. 9A, 9B & 9C: depict profile views with section planes and cross-section views of a fluid transfer device embodiment.

FIGS. 10A, 10B & 10C depict profile view with section plane, and cross-section views, and a perspective view a fluid transfer device embodiment.

FIGS. 12A, 12B & 12C depict profile view with section plane, a cross-section view and a perspective view of the device of FIG. 8.

FIGS. 14A, 14B & 14C depict profile view with section plane, a cross-section view of a flow device embodiment.

DETAILED DESCRIPTION

Figure 1:
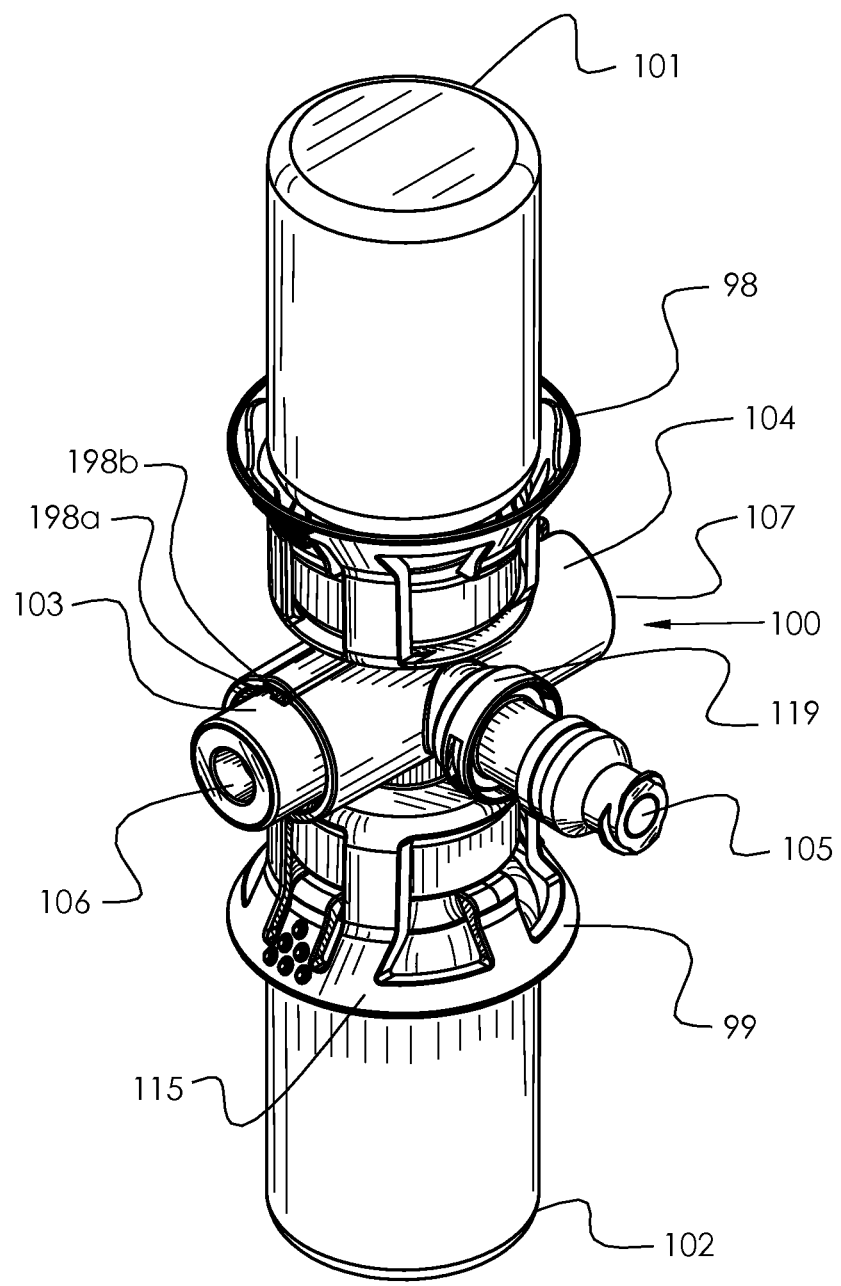
FIG. 1 is a perspective view of an aspect of a fluid transfer device as disclosed and described.

Throughout the specification, the term "fluid" as used herein is inclusive of gaseous, liquid, and combinations of gas and liquid medium unless specifically designated as limited to a particular medium.

Throughout the specification, the term "liquid" as used herein is inclusive of suspensions, oil-in-water emulsions, water-in-oil emulsions, and liquids with or without dissolved, dispersed, or contained solids irrespective of the size of the solids or the amount present.

Throughout the specification, the phrases "dual vial access device," "drug reconstitution device," "vial access device" and "fluid transfer device" are used interchangeably, unless otherwise stated, without any express or implied limitation to the scope of any claim. As is understood by one having ordinary skill in the art, a fluid transfer device provides for introduction of fluid from one vessel to another, while a fluid control device may include flow control means for diverting, metering, or interrupting flow between at least two flow paths.

Throughout the specification, the phrase "fluid transfer device" and the term "syringe" are used interchangeably unless otherwise stated, without any express or implied limitation to the scope of any claim, and are inclusive of any device with similar functionality to that of a syringe, but not necessarily the structure of a syringe.

Throughout the specification, the term "media" is inclusive of a solid, semi-solid, emulsion, liquid, or combination thereof. For example, the media can be a lyophilized drug.

Throughout the specification, the terms "shroud" and "skirt" are used interchangeably, unless otherwise stated, without any express or implied limitation to the scope of any claim.

Single Container Access and Fluid Transfer Device

In one aspect, a single container access and fluid transfer device provides a fluid path between a fluid source container and a transfer container, for example, a syringe. To access the fluid vial, the single vial access device is pressed down on top of the fluid source container for attaching, and/or retaining, and/or securing to the device. The central spike is designed to pierce the stopper/septum while simultaneously the shroud and its associated elements passes over the top of the vial. In one aspect, audio and/or tactile sensation is used as the container snaps in place. A syringe may then be attached to the luer port on top of the vial access device. The assembly is then inverted so that the fluid falls to the top end of the vial where the spike has penetrated the septum, and the syringe flow controller is drawn back, pulling liquid through the fluid lumen of the device from the vial into the syringe barrel. If the single vial access device is vented, then filtered air will enter the vial through the vent lumen and a neutral pressure will be maintained. If the single vial access device is not vented, then a slight vacuum will be created in the vial as the fluid is removed, and the user will need to hold the syringe flow controller back until it is removed for transfer.

Dual Container Access and Fluid Transfer Device

In one aspect, a dual container access and fluid transfer device is to provide a fluid path between a fluid source container and a media container in order to mix and/or reconstitute media, and as a means to transfer the media out of the device, for example, to a syringe. To accomplish this, a fluid vial is attached to the fluid container accessing assembly of the dual access device by pressing the device down on the top of the vial so that the central spike pierces the septum of the vial while simultaneously the ring shroud snaps over the top of the vial, for attaching, and/or retaining, and/or securing to the device. The media container accessing assembly of the device is then attached to the media vial in the same way. In one aspect, audio and/or tactile sensation is used as either or both containers snap in place. Visual indicia can be used in proximity to either shroud to indicate to a user which container should be attached. A pressure source port is configured on the device to accept a pressure source (such as a syringe), and the assembly oriented with the fluid vial vertically upwards. The fluid can then be drawn into the syringe from the fluid source. The slidably sealing flow controller may then be pressed to a second position in fluid communication with the media container, and the syringe can be emptied into the media container for mixing and/or reconstitution. Once mixed and/or reconstituted, the device may be reoriented with the media vial vertically upwards, and the media can be drawn into the syringe for transfer.

Slidably Sealing Flow controller

The slidably sealing flow controller provides for multiple fluid paths, and together with the pressure source port, allow the device to be used with alternative configurations of containers to accommodate various fluid sources and methods of operation, which may reduce inventories (and associated costs) without requiring complex manipulations from the user, which may reduce errors.

Venting

Vents increase the ease of use by relieving pressure that may build up in the fluid and media containers during transfer of volumes. One-way valves may be used for venting. Vent pathways may include a filter placed between the fluid transfer portions and the ambient surroundings. Such a filter may consist of a media with pores in the 0.2 micron size range, which is capable of blocking microorganisms from entering, and such filters may be hydrophobic, which are capable of blocking liquid from escaping. A hydrophobic filter may prevent leaking of liquid through the vent path, however the liquid that is prevented from escaping will also block the air flow. A single vent filter may be used in conjunction with the sliding valve mechanism changing fluid pathways to provide each media container with access to the vent selectively. Incorporating a vent filter in each end of the slidably sealing flow controller provides two separate vent paths, and allows each vent path to be accessed separately as required, reducing the chance of the vent being blocked by wetting of the hydrophobic filter. The device configurations described herein can function with venting, without venting, or with a combination of vented and unvented pathways. The filter media can be combined with one-way fluid control valves that are integral with the flow controller.

Shroud

The shroud feature of a vial access device serves two purposes. First, it supports and helps retain and/or secure the vial when the device is assembled. Second, it covers and protects the spike when the device is not attached to a vial. Previously reported shrouds consist of a number of tabs or fingers that are nominally in interference with the vial top diameter, and when assembled, deflect outwards until they pass the top section of the vial and then snap back in. In this configuration the strength of the vial retention is directly proportional to the force required to snap the shroud over the vial top. To achieve a secure vial retention force the assembly force can become uncomfortably high, which can lead to difficulty during use resulting in the user dropping containers during assembly of the device. In contrast, using the ring shroud configuration as disclosed and described herein, the main body of the shroud consists of a distal solid ring (annular edge) supported by segments projecting from a flat base. The ring and segments are slightly longer than the central spike that also projects from the housing, thus protecting the spike's point while in an unassembled state. Connected to and distally extending from the annular edge ring feature and positioned between the supporting segments, protrusions or fingers extend proximally toward the housing. Thus, in use, when a vial is received by the ring shroud, the protrusions deflect away from their initial position and the vial top and snap back to approximately their initial position when the closure portion of the vial passes the distal end of the protrusion. As a result, when a removing force is applied to the vial, the protrusions do not deflect away from the vial but instead deflect inwards and/or receive the force axially, preventing removal movement of the vial. Thus, the shroud configuration disclosed and described can provide a low container-to-device assembly force and a high retention force (or removal force) superior to previously reported shrouds. As such, the shroud disclosed and described herein can provide for single-use operation of containers and/or the device.

The transfer device for the transfer of fluids between containers herein disclosed and described can be configured in a variety of ways. The transfer device may be used in connection with the transfer of a fluid into a container in which there is a vacuum. The piercing members are designed to penetrate stoppers or septum sealing the containers.

The following is a description of the drawings and associated features of each aspect of the device and methods disclosed and described herein.

FIG. 1 depicts a perspective view of a first aspect device (100) of a shroud associated with a fluid transfer device. The shroud is depicted as generally ring shaped, but can be oval or of another shape. The device comprises a fluid container accessing assembly (98) for accessing a fluid container and a media container accessing assembly (99) for accessing a media container. The media in the container may be a solid, semi-solid, emulsion, liquid, or combination thereof. In one aspect, the media is a lyophilized drug. A slidably sealing flow controller (103), housing (104) providing a barrel for slidably receiving the flow controller, connector (119) having removable needle-less connector (105) for connecting a pressure source (which may be but is not limited to a standard syringe), check valve/filters (106, 107)) positioned in the interior of the flow controller. As shown, device (100) comprises fluid container accessing assembly (98) comprising shrouds (110, 117) each having a annular edge (115) for attaching, and/or retaining, and/or securing a fluid container and media container (102), which may be a vial (as shown) having a closure portion with septum/stopper, an IV bag, or other container.

Figures 2A, 2B:
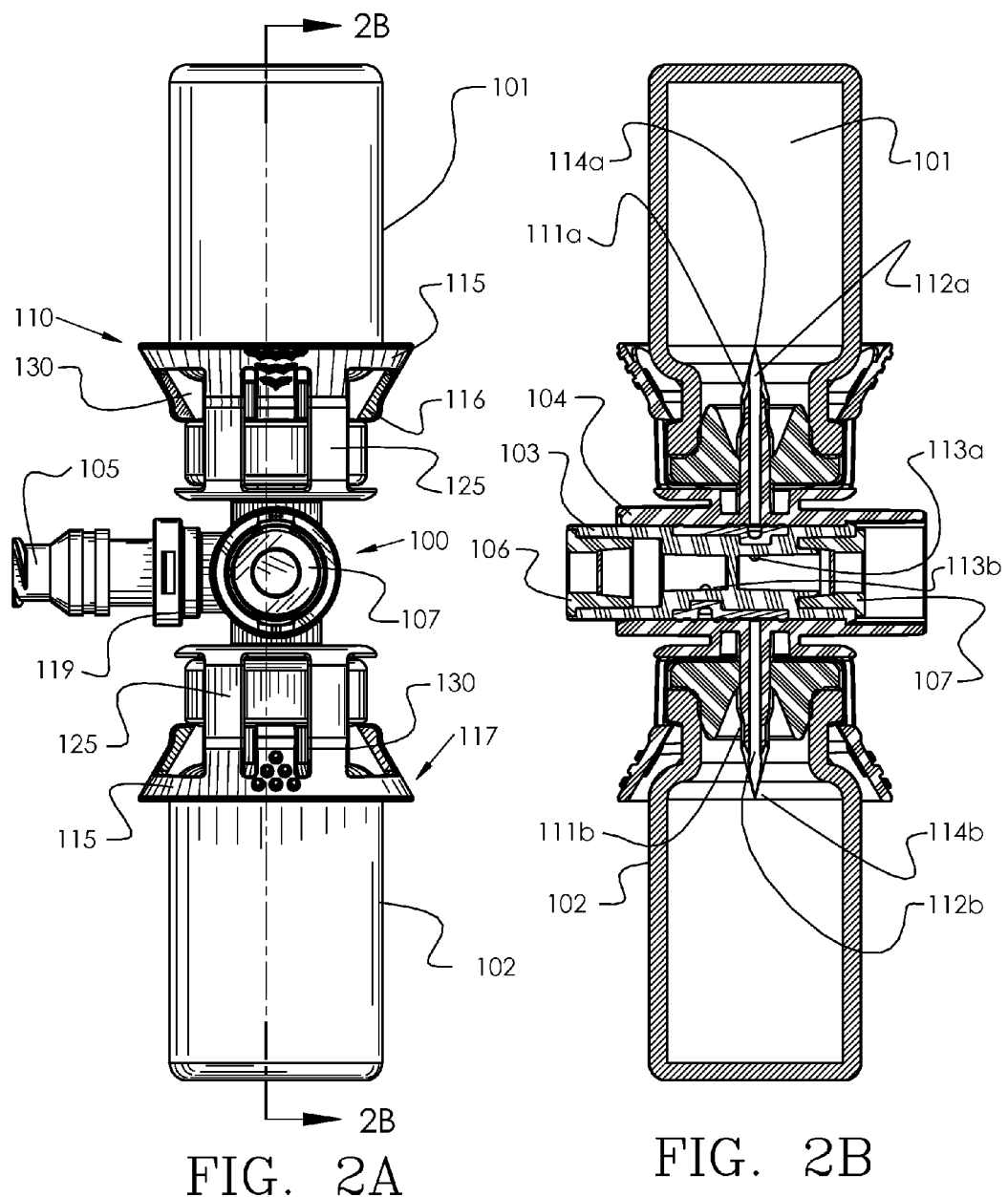
FIGS. 2A & 2B depict a profile view with a section plane and a cross-section view respectively, of the device of FIG. 1, with a slidably sealing flow controller in a first position.

FIGS. 2A & 2B depict a profile view with a section plane and a cross-section view of the FIG. 1 aspect configured for vial-to-vial reconstitution, with the slidably sealing flow controller in a first position. Spikes (111a, 111b) are disposed within piercing assemblies corresponding to the container (fluid container accessing assembly and media container accessing assembly). The spikes provides for accessing (e.g., piercing) a stopper or septum of the closure portion and comprises at least one fluid lumen (112a, 112b), and for accessing at least one vent lumen (113a, 113b) and at least one spike distal end (114a, 114b). In one aspect, the vent lumen(s) is in fluid communication with the ambient surrounding the device via the interior of the flow controller. In another aspect, the vent lumen is in fluid communication with the ambient surrounding the device and includes at least one filter (106, 107) at a point along is passageway fluidically coupled with the slidably sealing flow controller (103) interior. In one aspect, shroud (110, 117), of any cross-sectional geometry about its interior, comprises at least one annular edge (115) distally extending from the housing by a plurality of connecting segments (125) defining a corresponding plurality of openings (130), and a plurality of protrusions (116), each protrusion having a proximal end adjacent or attached to the annular edge and a distal end positioned in the opening that provides for attaching, and/or retaining, and/or securing a vial or other container and provides for resistance against vial/container removal. As shown, device (100) optionally comprises a second shroud (117) of the same configuration as the shroud (110) of the fluid container accessing assembly for attaching to a media container (102).

Figure 3A:
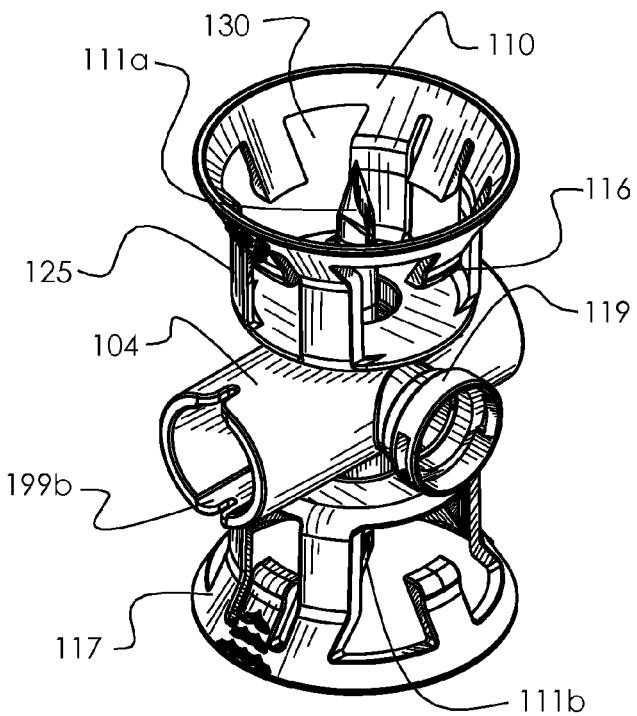
FIGS. 3A, 3B and 3C are a perspective view, a sectional plane, and corresponding cross-sectional view of a shroud for a fluid transfer device as disclosed and described.
Figure 3B:
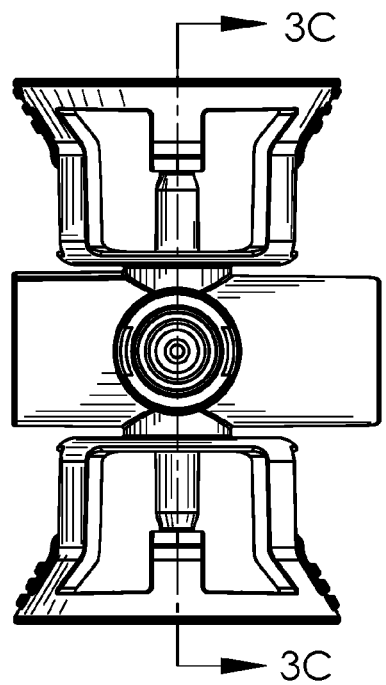
Figure 3C:
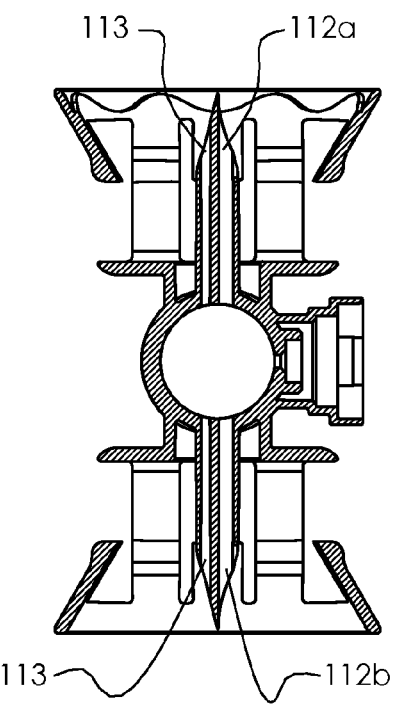

FIGS. 3A, 3B and 3C are a perspective, profile view with a section plane, and a cross-section views, respectively of device (100) of FIG. 1. Housing (104) comprising flow controller-receiving barrel, shrouds (110, 117), corresponding spikes (111a, 111b) with fluid lumens (112a, 112b) and vent lumens (113), and connector (119). Alignment keyway (199b) in housing barrel accepts corresponding features of flow controller to prevent rotation about barrel and for preventing the flow controller from sliding completely out from the barrel, as discussed further below.

Figure 4B:
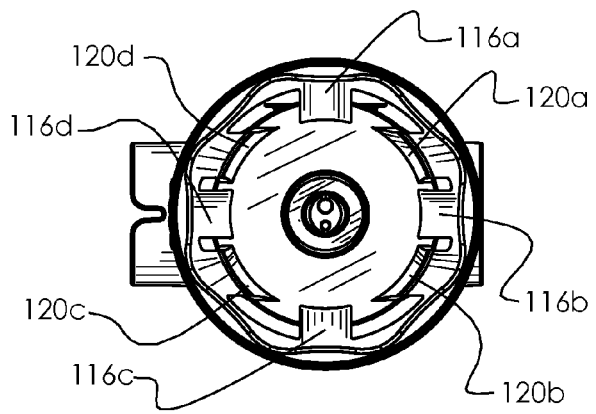
FIGS. 4A, 4B, 4C, and 4D depict orthographic views of the device of FIG. 3.
Figure 4A:
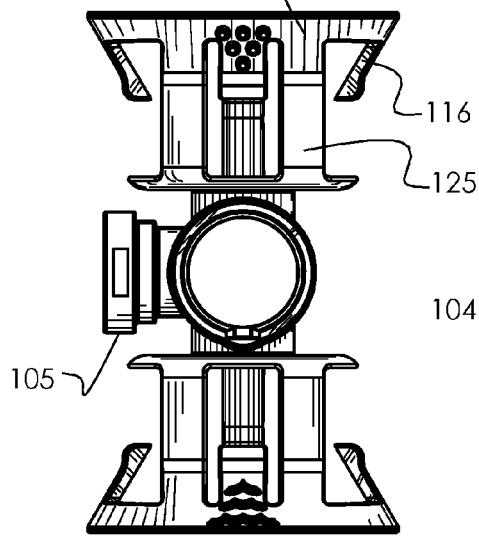
Figure 4C:
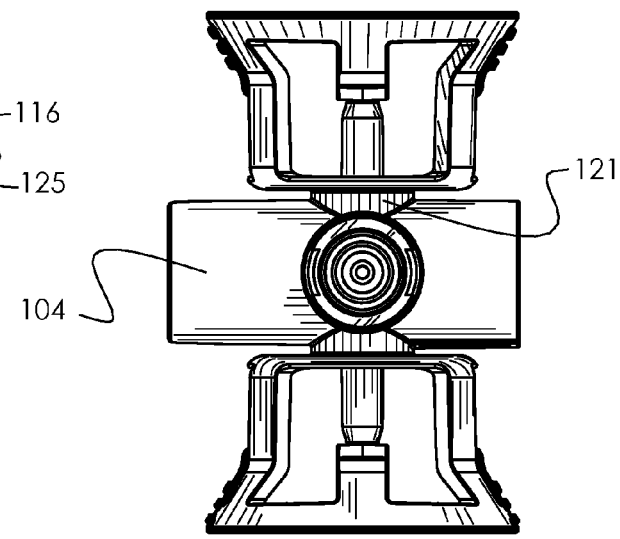
Figure 4D:
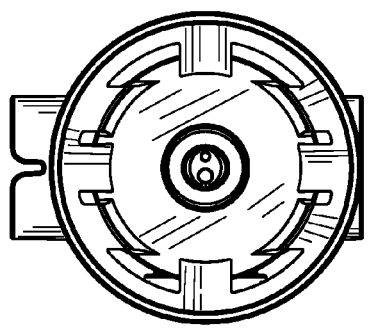

FIGS. 4A, 4B, 4C & 4D are orthographic views of the main component of the device of FIG. 3. Details of the shroud configuration illustrated are the annular edge (115) which essentially encircles the closure portion of a container and supports the retaining/receiving protrusions (116). In a preferred aspect, there are four protrusions (116a), (116b), (116c) & (116d) positioned approximately opposite of one another as shown in FIG. 4B with four openings defined by four segments (120a), (120b), (120c) & (120d) connect the annular edge (115) to the housing of the shroud, which in one aspect is attached to the housing (104) by post (121). In another aspect, the shroud is integral with the central barrel. FIG. 4D shows a view of the shroud which is a mirror image of opposing shroud described above. The shrouds can be arranged such that they are diametrically opposed in relationship to the housing as shown, or they may be arranged in alternate configurations, such as perpendicular to each other. Other arrangements of the shrouds are envisaged.

Figures 5A, 5B:
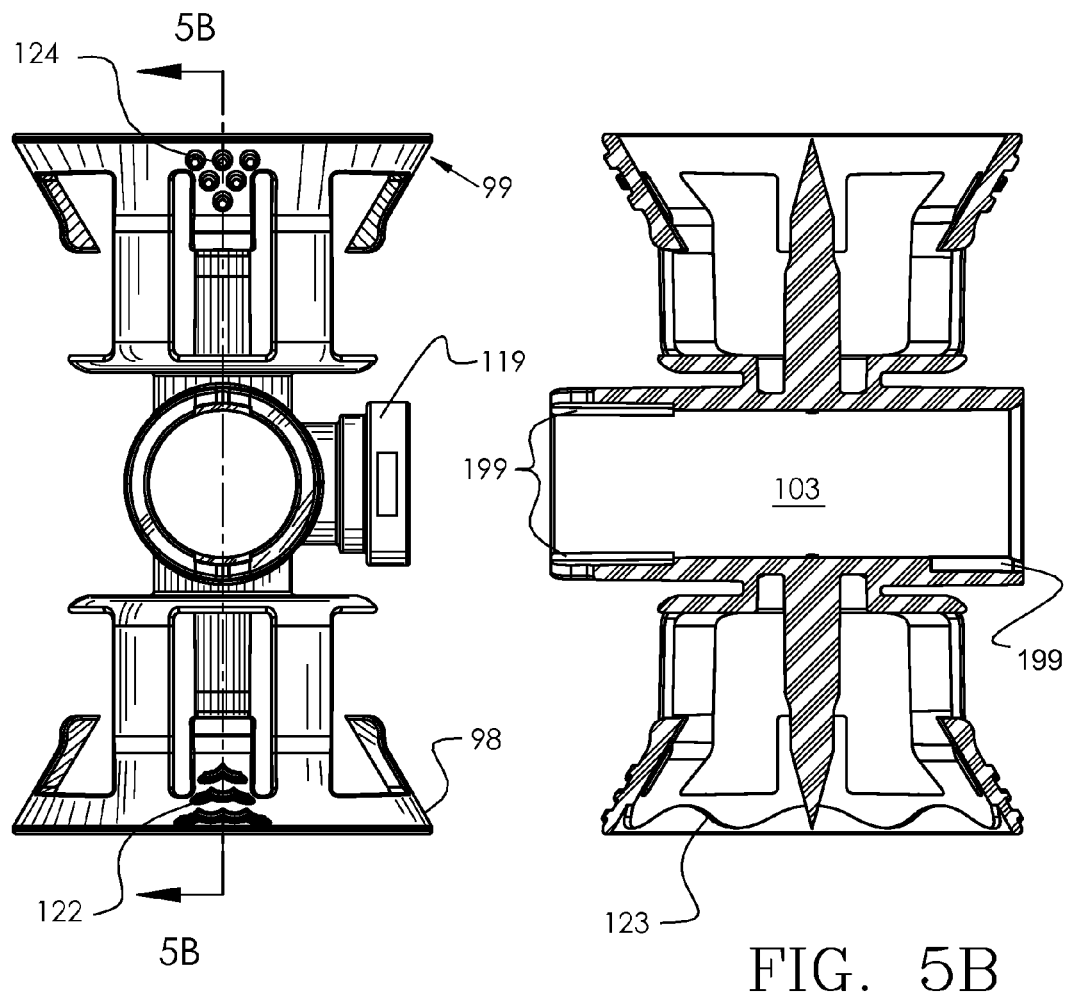
FIGS. 5A & 5B depict a sectional plane and corresponding cross-sectional view, respectively, of the device of FIG. 3.

FIGS. 5A & 5B are a side view and a section views, respectively, of the device of FIG. 3. Indicia (122, 123, 124) may be placed on the one or both shrouds to help the user identify the proper end of the device for attaching the fluid container and/or media container. In one aspect, symbols or colors can be used as indicia. Other indicia can be used, such as raised or depressed areas. FIG. 5B depicts keyways (199) for orientation control of flow controller (103) and for preventing release of the flow controller from housing.

Figure 6A:
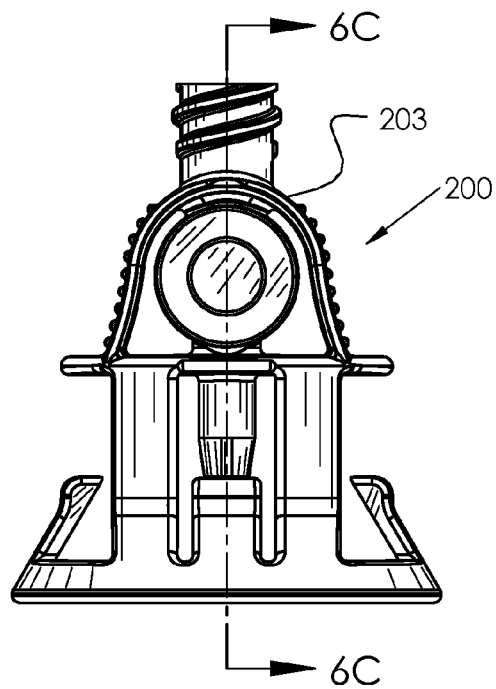
FIGS. 6A, 6B & 6C depict a front view, a side view and a section view, respectively, of a second aspect of a ring shroud.
Figure 6B:
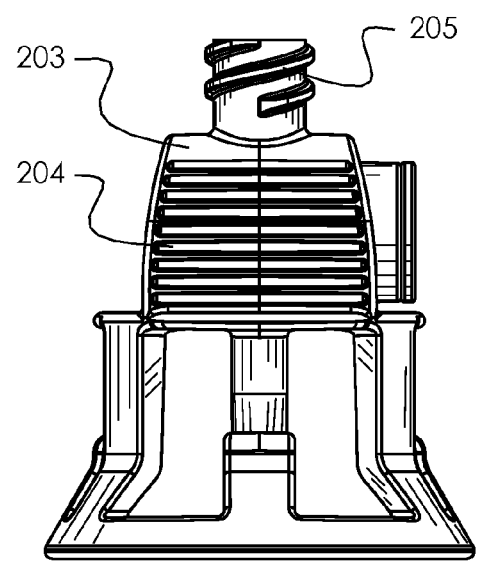
Figure 6C:
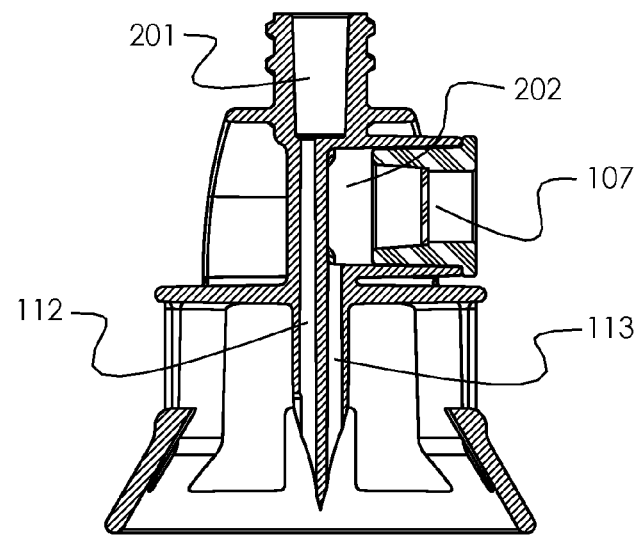

FIGS. 6A, 6B & 6C are a front view, a side view and a section view of a second embodiment shroud (200) of a ring shroud adapted for use with a single container. The features of the ring shroud and the spike are the same as those of device (100) described above, however, above the shroud, fluid lumen (112) from the spike transitions into a luer connection (201) for attaching a fluid delivery device, such as a syringe. Vent lumen (113) is connected to housing (202) providing fluid communication with the ambient surroundings and may contain a vent and/or filter (107). Surface (203) is provided for the user to grip the vial adapter comprised of parallel raised features (204) on the surface acting as gripping means. External threads of standard luer configuration (205) allow for releasable, secure syringe attachment.

FIGS. 7A, 7B & 7C are a front view, a side view and a section view of a third embodiment shroud (300) which is unvented and configured for adapting to a single container. Spike (302) is configured with a single, central fluid lumen (301) with offset point. As shown, the fluid lumen transitions into a luer connection (303) for attaching a syringe. Other connections can be used, such as threaded connections. Surface (304) is provided for the user to grip the vial adapter and parallel features on the surface act as a gripping means. External threads of standard luer configuration (306) allow for releasable, secure syringe attachment.

Figure 8:
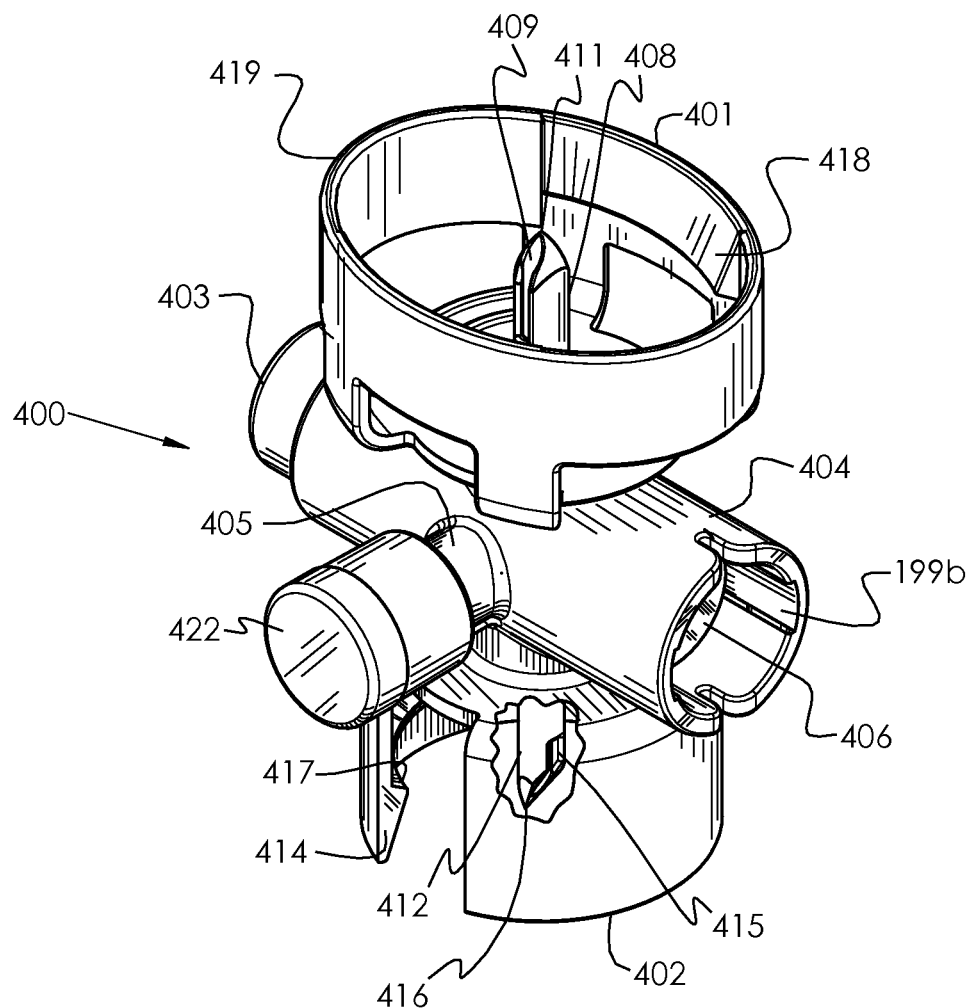
FIG. 8 is a perspective view of a fluid transfer device embodiment.

FIG. 8 is a perspective view of a fluid transfer device embodiment reconstitution device (400) with partial sectional view showing additional container accessing means. The device comprises opposing accessing means (e.g., spikes) for accessing containers. Flow controller (403) is slidably received by barrel in housing (404). Connector (405) provides for connecting a pressure source (e.g., standard syringe) covered by connector cap (422). Check valve/filter (406) is positioned at either opposing ends of the flow controller. Keyway (199b) in housing barrel accepts corresponding key features of flow controller (198b, 199a FIG. 14C) providing alignment, anti-rotation, and prevention of release from barrel. Shrouds (401, 402) opposely project from housing (404) and essentially surround container accessing means, shown as spikes (408, 412). Spikes (408, 412) terminating at spike distal ends (411, 416). Spikes can comprises an open slot (409) in lumen to assist in complete removal of the contents of container. Shrouds are depicted with annular ring (418) or with at least one slit (414), of a cross-sectional geometry about its interior suitable for a particular container, and an elliptical cross-section (419) which may allow for attachment to fluid containers of variable diameters. Shroud may have at least one attachment means (417) of any cross-sectional geometry disposed about its interior in an annular-like fashion.

Other geometries of shroud can be used. Previously described shroud of device (100) can be substituted for the shroud depicted in FIG. 8. Connector (405) is positioned between the first and second ends of housing barrel may comprise a locking means for sealably connecting to the external pressure source or, as depicted, can be fluidically sealed by cap (422). Vent lumen is in fluid communication with the ambient surrounding the device via the interior of the slidably sealing flow controller and can be adapted to an optional check valve/filter (406) at a point along its passageway coupled with the slidably sealing flow controller (403) as depicted. Filter and vent components can be provided on either or each end of the flow controller.

FIGS. 9A, 9B & 9C: depict profile views with section planes and cross-section views of the device (400), shown configured for IV bag-to-vial fluid transfer and media reconstitution. Slidable flow controller (403) is disposed between the first and second ends of barrel formed in housing. Controller comprises a plurality of fluid channels (420, 420a) and vent conduit (410a,) to selectively provide fluid communication between the IV bag, connector (405) and the media container, and optionally vent. FIG. 9A depicts the device with the slidably sealing flow controller in a first position, wherein fluid communication is provided between the connector, a vent conduit, and the IV bag, with spike (408) penetrating septum (497) of IV bag (499) and shroud (407) securably engaged with the IV bag about the septum. A media container is also depicted engaged with device (400). Spike includes at least one fluid lumen (408a), at least one vent lumen (408b) terminating proximal to spike distal end (411). Vent lumen (408b) is in fluid communication with the ambient surrounding the device via vent conduit (410a) accessing interior of the slidably sealing flow controller. Optional check valve/filter (406) at a point along its passageway is fluidically coupled with the interior of slidably sealing flow controller (403) as in the depicted embodiment. Filter and vent components can be provided on each end of the flow controller, for example, to provide venting during fluid transfer to either container.

Connector (405) is slidably disposed in housing and can comprise a locking means for sealably connecting to the external pressure source or may be sealed by a cap (422). When the connector is sealed by a cap, its interior provides a path via connector lumen (421) for providing fluid communication between the containers through the flow controller channels (420, 420a). Alternatively, when the connector is connected to the external pressure source, the luer connector of the external pressure source blocks the connector lumen (421), providing fluid communication essentially through the external pressure source and between the media container.

FIGS. 10A, 10B & 10C depict profile view with section plane, and cross-section views, and a perspective view, with the slidably sealing flow controller in its second position wherein the fluid communication is provided between the connector and the media container (102). In this second position, the slidably sealing flow controller (403) is configured such that it does not allow fluid communication between the IV bag and the media container. Vent conduit (410a) is no longer visible in cross section view of FIG. 10B as it has moved off alignment with vent lumen (408b).

Figure 11A:
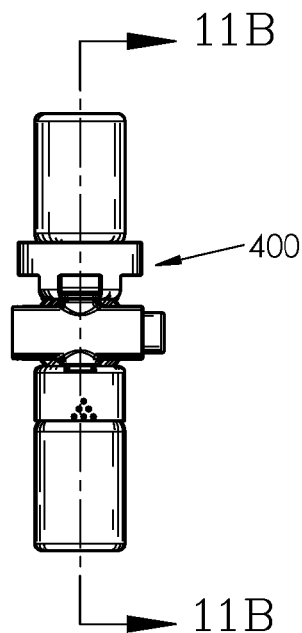
FIGS. 11A, 11B & 11C depict profile view with section plane, perspective view, and cross-section view of the device of FIG. 8.
Figure 11C:
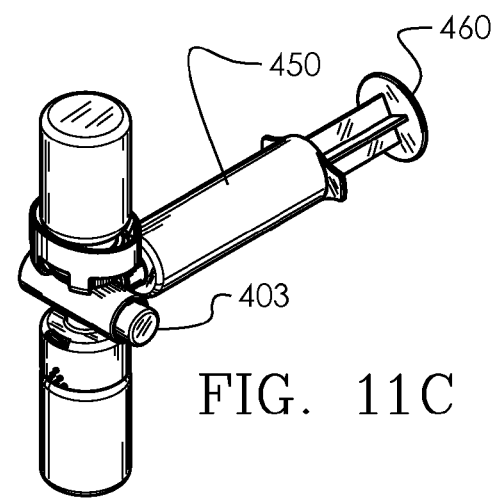
Figure 11B:
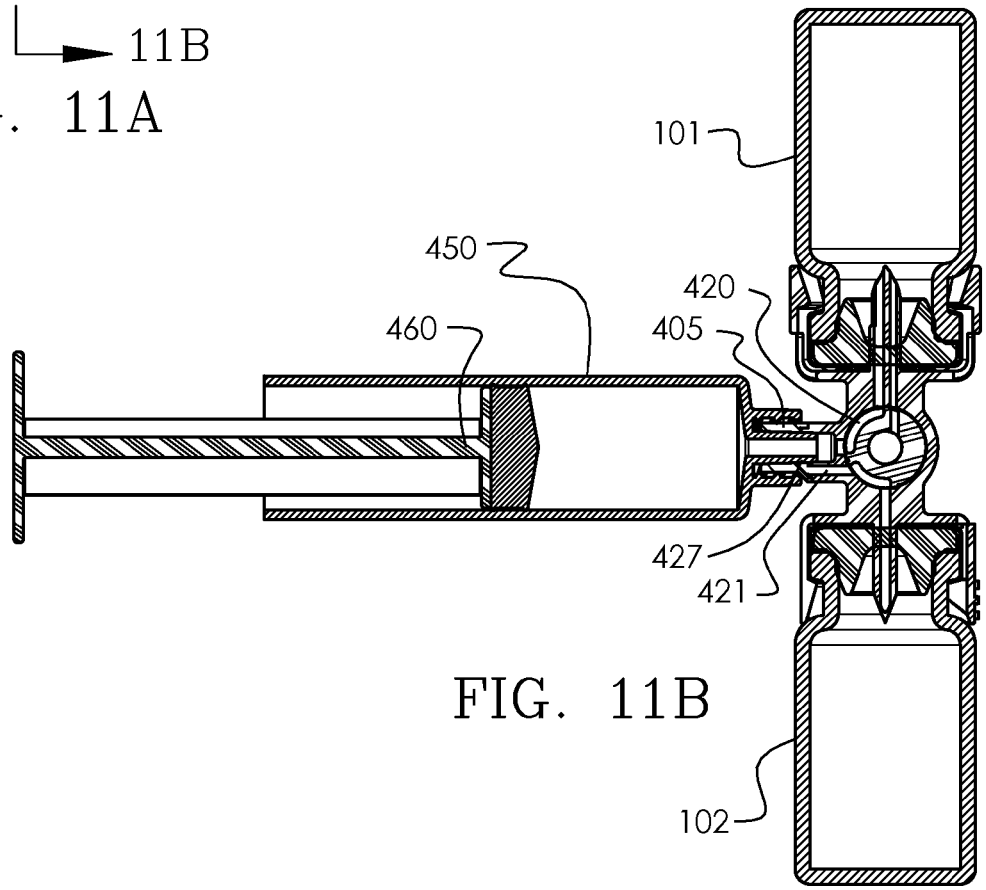

FIGS. 11A, 11B & 11C depict profile view with section plane, perspective view, and cross-section view of the device of FIG. 8 configured for vial-to-vial reconstitution with the slidably sealing flow controller in the first position. In this configuration, connector (405) disposed between the first and second ends may be attached by locking means for sealably connecting to an external pressure source, in this case, syringe (450). Luer connector (427) of the syringe blocks connector lumen (421) and, in combination with the flow controller fluid channel (420), creates a fluid communication between fluid container (101) and the syringe. Withdrawing the syringe plunger (460) draws fluid from the fluid container into the syringe body so that a metered amount of fluid can be withdrawn from the fluid container.

FIGS. 12A, 12B & 12C depict profile view with section plane, a cross-section view and a perspective view of the device of FIG. 8 configured for vial-to-vial reconstitution with the slidably sealing flow controller in the second position. In this configuration, as in the first position, luer connector (427) of the syringe blocks connector lumen (421) and, flow controller fluid channel (429), creates a fluid communication between the media container and syringe (450). Advancing syringe plunger (460) sends a metered amount of fluid from the syringe body into the media container for reconstitution or dilution, etc.

Figure 13A:
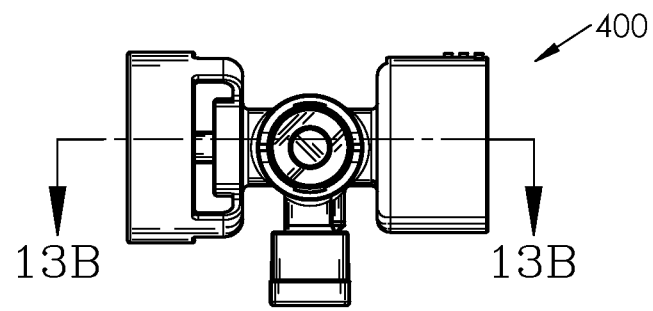
FIGS. 13A & 13B: These figures provide a profile view with section plane and a cross-section view of a fluid transfer device embodiment.
Figure 13B:
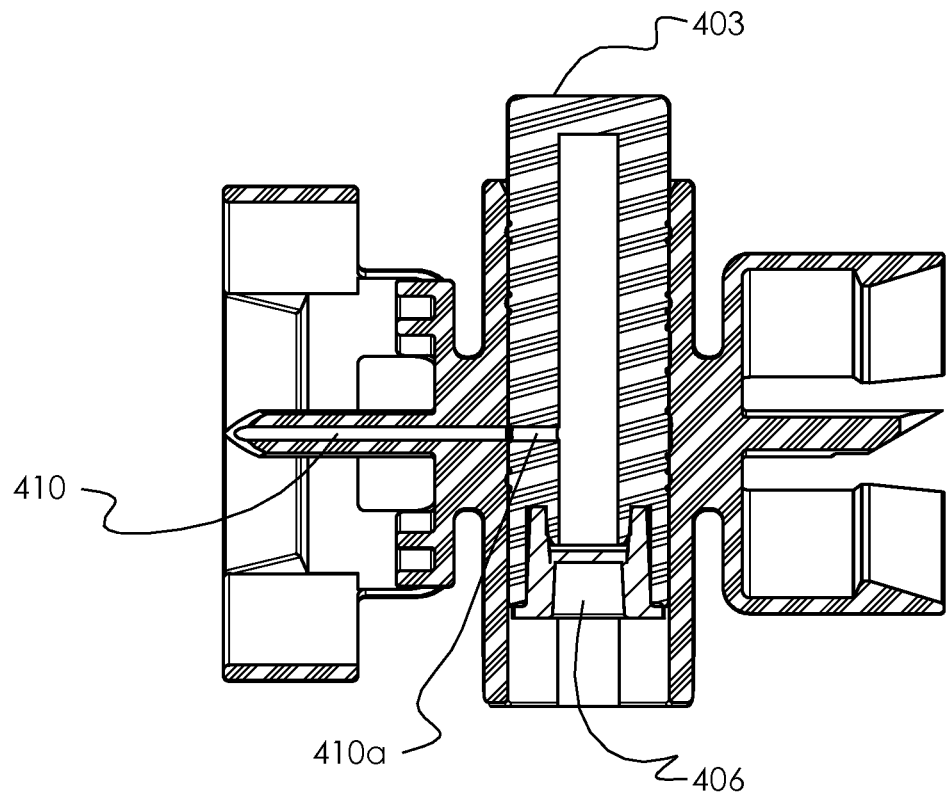

FIGS. 13A & 13B: These figures provide a profile view with section plane and a cross-section view of device (400), showing vent conduit (410a) in fluidic communication with the interior of flow controller (403) and in fluidic communication with check valve/filter (406). Vent lumen (408b) of spike, in combination with vent conduit (410a) in the flow controller (403) comprises a vent path between vent lumen and the ambient surrounding. Filter (406) may be disposed in this pathway. In the second position of the slidably sealing flow controller this pathway is disabled.

FIGS. 14A, 14B & 14C depict profile view with section plane, a cross-section view of a flow device (500) embodiment, and a perspective view of an alternative flow controller (503) embodiment, respectively. Flow controller (503) may be disposed between opposing ends of hosing (504). Controller contains vent channels (523a, 524) in fluid communication with corresponding vent conduits (523a', 523') providing access to the interior of the flow controller, and fluid channels (524, 524a), to selectively provide fluid communication between the connector and/or the lumens of container accessing assemblies. Check valve and/or filter (506) is optionally disposed within the interior of the flow controller. Housing (504) may have at least one cutout (525) for relieving pressure buildup from flow controller actuation.

Fluid container accessing assembly (501) includes shroud (507) for attaching to a fluid container and having at least one slit (514), and a plurality of spikes (508, 508a) disposed therein for a penetrating a container septum and accessing fluid. The shroud includes annular ring (518) of any cross-sectional geometry about its interior. Fluid lumen (510a), and vent lumen (510b) terminate in proximity to corresponding spike distal ends (511, 511a). Vent lumen (510b) is in fluid communication with the ambient surrounding the device and optional check valve/filter (506) at a point along the interior passageway of controller (503), which is fluidically coupled with vent channel (524a) and vent conduit (523) of controller (503).

Media container accessing assembly (502) comprise shroud (513) having at least one attachment means (534) of any cross-sectional geometry disposed about its interior in an annular-like fashion for attaching to a media container and having at least one opening or slit (530), and a plurality of spikes terminating at distal ends (531, 531*a*) disposed therein. Fluid lumen (532*a*), and vent lumen (532*b*) terminate proximal to corresponding spike distal ends (531, 531*a*) of each. Vent lumen (532*b*) is in fluid communication with the ambient surrounding the device and optional check valve/filter (506) at a point along the interior passageway of controller (503), which is fluidically coupled with vent channel (523) and vent conduit (523') of controller (503). Connector (505) disposed between the first and second ends comprises a locking means for sealably connecting to the external pressure source, e.g. a syringe.

Figure 15:
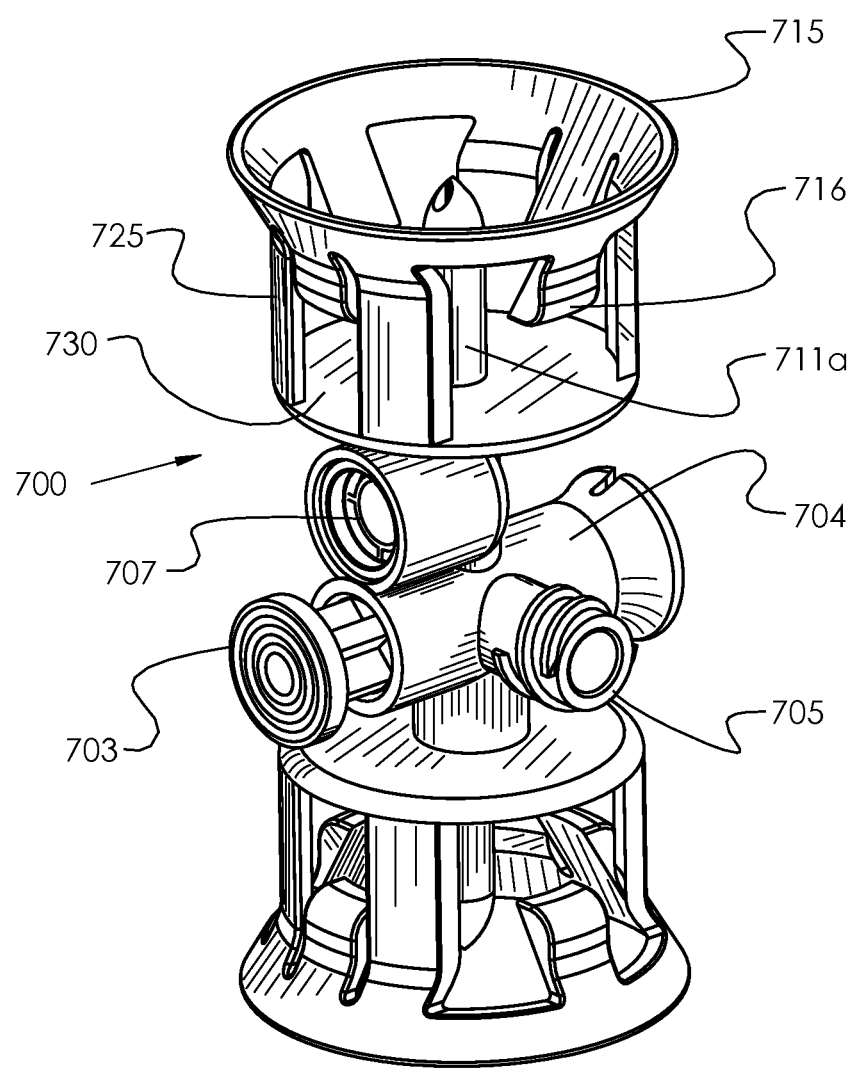
FIG. 15 depicts a profile view of a fluid transfer device embodiment.

FIG. 15 depicts a fluid transfer device (700) having shroud of configuration as above for device (100) except venting is provided via vent (707) integrated into housing (704). Thus, shroud comprises at least one annular edge (715) distally extending from the housing by a plurality of connecting segments (725) defining a corresponding plurality of openings (730), and a plurality of protrusions (716), each protrusion having a proximal end adjacent or attached to the annular edge and a distal end positioned in the opening that provides for attaching, and/or retaining, and/or securing a vial or other container and provides for resistance against vial/container removal. Shroud encircles spike (711*a*). As shown, device (700) optionally comprises a second shroud of the same configuration as above for attaching to a media container.

Methods of Use

At least one purpose of the disclosed fluid transfer device is to provide a fluid path between a fluid source container and a media container in order to reconstitute the media. The device provides alternative methods to accomplish this.

1) If exact control of the fluid source is not required, the device may be used with the cap in place on the pressure source port. The user connects a first container, such as a fluid source container to one end of the device, and a second container, such as a reconstitutable media container to the opposing end of the device, as specified in the figure descriptions. The slidably sealing flow controller may then be urged to a second position, which fluidically connects the first and second containers, and the media is reconstituted. The slidably sealing flow controller may then be returned to the first position to isolate the media container if desired.

2) If exact control of the fluid dose is required, a pressure source (such as a syringe) may be attached to the pressure source port. This attachment interrupts the fluid path in the connector, and the fluid can then be drawn into the syringe from the fluid source. The slidably sealing flow controller may then be pressed to a second position in fluid communication with the media container, and the syringe can be emptied into the media container for reconstitution. Once reconstituted, the fluid and media may be drawn again into the syringe for administration.

Venting during fluid transfer independently between one or both of the fluid container or the media container is possible via the at least one check valve/filter arrangement in the interior of the flow controller. If desired, the venting during fluid transfer can be disabled in the flow controller.

Thus, in at least one aspect, a method of transferring material among containers comprises providing a fluid transfer device, the device comprising a housing including a connector, the housing adapted to receive a fluid container. A flow controller at least partially slidably disposed in the housing and is positionable between first and second positions. The flow controller comprises at least one fluid channel, and at least one vent conduit. At least one container is received by the housing of the fluid transfer device, and the flow controller is slidably positioned to the first position to provide fluidic communication between the at least one fluid channel and the at least one vent conduit and the fluid container. The housing is adapted to also receive a media container comprising a pharmaceutical in the form of a solid, liquid, suspension, or combinations thereof. The flow controller is configured within the housing and slidably disposable to one of the following positions:

a first position wherein the at least one fluid channel and at least one vent conduit are in fluid communication with the fluid container, the vent conduit, and the connector;

a second position wherein the at least one fluid channel is in fluid communication with the media container and with the connector, and not in fluid communication with the at least one vent conduit.

Modification and Alternative Aspects

Modifications and alternatives of the above aspects relating to the device and its components are envisaged. An exemplary listing of such modifications and alternatives is provided below.

Gripping

In the drawings and descriptions, gripping can be included about the exterior surface of the device. Gripping can be any of a number of surface effects including, but not limited to, embossed or de-bossed features, surface finish and overmolded or two-shot features.

Standard Syringe Interface

The aspects described herein can be designed such that they are able to mate with standard and non-standard off-the-shelf syringes. This can be accomplished via standard luer configurations or this can potentially be a cost reduction measure because tooling will not be required for one or more of these components. The final device can also be substantially affixed to the syringe.

Multiple Spikes

Any aspect of the described device can allow for spike lumens to be contained within their own spike. Any of the spikes can be integrated with their respective components or they can be assembled and thereby can be of a different material that can include but is not limited to plastics and metals.

Alternate Attachment Means

The aspects described herein can alternately be equipped with other attachment means in combination with the described shroud aspects for attaching, and/or retaining, and/or securing various containers, such as but not limited to, diluent bags and vials.

Alternate Access Means

The aspects described herein can alternately be equipped with other access means for mating and sealably connecting to various containers such as but not limited to diluent bags and vials.

Cap

A cap or other suitable covering element can be applied to the connector such that in the event that a pressure source is not needed or not desired to be used with to the device prior to connecting media containers, regardless of whether the slidably sealing flow controller of the device is in the first or second position.

Manufacturing

Adhesives can be employed to substantially join components, particularly attachments that can be coupled with luer connections, where applicable. Adhesives can be but are not limited to: cyanoacrylate, 2-part epoxy, heat-activated resin, UV cured adhesive and hot melt. Joining can also be achieved through, but not limited to, the use of solvent bonding, ultrasonics and heat-staking means. All of the proposed aspects can be injection molded. Design intent can be such that designs are molded with simple open/close tooling to reduce tool cost and cycle times.

Where feature definition can not be able to be achieved by single tool molding; ultrasonic welding, adhesives or mechanical retention can be employed to join components. Furthermore, where dissimilar materials can be advantageous, a two-shot molding technique can be utilized.

The phrases "capable of" and "adapted for" and "configured for" as used herein, when referring to recitation of function associated with a recited structure, is inclusive of all conditions where the recited structure can actually perform the recited function. For example, the phrase "capable of" includes performance of the function under normal operating conditions, experimental conditions or laboratory conditions, as well as conditions that may not or cannot occur during normal operation.

The term "comprising" and its grammatical equivalents, as used herein is synonymous with "including," "containing," or "characterized by," and is inclusive or open-ended and does not exclude additional, unrecited elements or method steps. As used herein, "consisting of" and grammatical equivalents thereof exclude any element, step, or ingredient not specified in the claim. As used herein, "consisting essentially of" and grammatical equivalents thereof limit the scope of a claim to the specified materials or steps and those that do not materially affect the basic and novel characteristic or characteristics of the claimed invention.

While the invention has been described in detail and with reference to specific embodiments and aspects thereof, it will be apparent to one skilled in the art that various changes and modifications can be made without departing from the spirit and scope of the claims.

We claim:

1. A container accessing assembly comprising:
   a housing with a container accessing member;
   at least one shroud projecting from the housing and surrounding the container accessing member, the shroud comprising:
   a plurality of segments terminating in a continuous annular edge, the plurality of segments together with the annular edge defining a plurality of openings;
   a plurality of protrusions, each of the plurality of protrusions projecting from the annular edge and terminating at a distal end positioned in one of the plurality of openings, the distal ends inwardly extending, the plurality of protrusions together with the annular edge defining a receiving volume sized to accommodate a closure portion of a container.

2. The container accessing assembly of claim 1, wherein the plurality of protrusions are in a fixed position with respect to the annular edge.

3. The container accessing assembly of claim 1, wherein at least one of the protrusions has a tapered edge at the distal end thereof.

4. The container accessing assembly of claim 1, wherein the plurality of protrusions has a tapered edge at the distal end thereof.

5. The container accessing assembly of claim 3, wherein the tapered edge tapers outward proximate the distal end of the at least one protrusion.

6. The container accessing assembly of claim 1, wherein a distance is maintained between the distal end of the plurality of protrusions and housing and the distance is dimensioned to allow for receiving a closure portion of a container.

7. The container accessing assembly of claim 1, wherein a distance is maintained between the plurality of segments and the plurality of protrusions, and wherein the distance is dimensioned to allow the protrusions to flex when receiving a closure portion of a container.

8. The container accessing assembly of claim 1, wherein the plurality of segments are substantially parallel relative to each other.

9. The container accessing assembly of claim 1, wherein the plurality of segments each have at least one straight edge along their respective longitudinal axis.

10. A shroud for connecting to a container having a closure portion, the shroud comprising:
    a housing with a container accessing member;
    a plurality of segments terminating in a continuous annular edge and defining a plurality of openings, the continuous annular edge surrounding the container accessing member;
    a plurality of protrusions circumferentially spaced and inwardly extending from the annular edge, the protrusions defining a receiving volume dimensioned to receive a closure portion of a vial, wherein each of the protrusions have a proximal end connected to the annular edge and a distal end positioned in one of plurality of openings,
    whereby the protrusions deflect outwardly away from an initial position during contact and traversing of a closure portion of a vial and return to approximately their initial position when the closure portion of the vial passes the distal end of the protrusion,
    whereby the protrusions deflect inwardly towards a closure portion of a vial when a removing force is applied to the vial, thereby preventing removal of the vial.

11. The shroud of claim 10, wherein the housing comprises an opposed pair of each of the plurality of segments and the plurality of protrusions.

12. A fluid transfer device, comprising:
    a housing adapted to receive a fluid container and a media container;
    a flow controller having an interior and an exterior, the flow controller at least partially slidably disposed in the housing, the flow controller comprising at least two fluid channels, at least one vent conduit, and a vent;
    a connector coupled to the housing and configured for fluid communication with the at least one fluid channel of the flow controller; and
    at least one shroud projecting from the housing, the shroud comprising:
    a plurality of segments terminating in a continuous annular edge and defining a plurality of openings;
    a plurality of protrusions, each of the plurality of protrusions projecting from the annular edge and terminating at a distal end positioned in one of the plurality of openings, the distal ends inwardly extending, the plurality of protrusions together with the annular edge defining a receiving volume sized to accommodate a closure portion of one of the fluid container or the media container;
    wherein the flow controller is configured to slidably move between a first predetermined position wherein at least one of the fluid channels provides fluid communication between the fluid container and the connector, and a second predetermined position wherein at least one of the fluid channels provides fluid communication between the media container and the connector.

13. The fluid transfer device of claim 12, wherein the vent conduit is in fluid communication with the interior of the flow controller.

14. The fluid transfer device of claim 12, wherein the vent conduit is in fluid communication with a vent integrally positioned within the interior of the flow controller.

15. The fluid transfer device of claim 12, wherein the housing comprises a keyway and the flow controller comprises a corresponding key, whereby the flow controller is restricted or prevented from rotation relative to the housing.

16. The fluid transfer device of claim 15, wherein the flow controller is restricted or prevented from slidably releasing from the housing.

17. The fluid transfer device of claim 12, further comprising:
- a fluid container accessing assembly associated with the housing, the fluid container accessing assembly adapted for accessing the fluid container, the fluid container accessing assembly comprising a fluid container piercing member and at least one fluid lumen, optionally in combination with a vent lumen and/or a filter; and
- a media container accessing assembly associated with the housing, the media container accessing assembly adapted for accessing the media container, the media container accessing assembly comprising a media container piercing member and at least one fluid lumen, optionally in combination with a vent lumen and/or a filter.

18. The fluid transfer device of claim 12, further comprising a removable member adapted to engage the flow controller such that the flow controller is prevented from moving prior to first use.

* * * * *